(12) United States Patent
Okada et al.

(10) Patent No.: US 12,187,982 B2
(45) Date of Patent: Jan. 7, 2025

(54) MIXTURE OF HIGHER SECONDARY ALCOHOL ALKOXYLATES WITH DIFFERENT CARBON CHAIN LENGTHS AND METHOD FOR PRODUCING SAME

(71) Applicant: NIPPON SHOKUBAI CO., LTD., Osaka (JP)

(72) Inventors: Atsushi Okada, Kawasaki (JP); Toru Inaoka, Kawasaki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 470 days.

(21) Appl. No.: 17/753,973

(22) PCT Filed: Sep. 23, 2020

(86) PCT No.: PCT/JP2020/035665
§ 371 (c)(1),
(2) Date: Mar. 18, 2022

(87) PCT Pub. No.: WO2021/060230
PCT Pub. Date: Apr. 1, 2021

(65) Prior Publication Data
US 2022/0364019 A1 Nov. 17, 2022

(30) Foreign Application Priority Data

Sep. 25, 2019 (JP) ................. 2019-173623
Sep. 25, 2019 (JP) ................. 2019-173624
Sep. 25, 2019 (JP) ................. 2019-173625

(51) Int. Cl.
| C11D 1/825 | (2006.01) |
| C07C 43/16 | (2006.01) |
| C11D 1/72 | (2006.01) |

(52) U.S. Cl.
CPC ............... *C11D 1/72* (2013.01); *C07C 43/16* (2013.01); *C11D 2111/12* (2024.01)

(58) Field of Classification Search
CPC ............ C11D 1/722; C11D 1/72; C11D 1/825
See application file for complete search history.

(56) References Cited

U.S. PATENT DOCUMENTS

| 2,870,220 | A |   | 1/1959 | Carter |           |
|-----------|---|---|--------|--------|-----------|
| 3,350,462 | A |   | 10/1967| Leary  |           |
| 4,166,039 | A | * | 8/1979 | Wise   | C11D 11/02 |
|           |   |   |        |        | 510/452   |
| 4,206,063 | A |   | 6/1980 | Wang   |           |
| 6,610,775 | B1|   | 8/2003 | Oharu et al. | |
| 6,624,268 | B1|   | 9/2003 | Maekawa et al. | |
| 2003/0176745 | A1 | | 9/2003 | Maas | |
| 2010/0267844 | A1 | | 10/2010 | Varineau et al. | |

FOREIGN PATENT DOCUMENTS

| GB | 1489694 A | 10/1977 |
| JP | S49-102608 A | 9/1974 |
| JP | 50-123704 A | 9/1975 |
| JP | S63150389 A | 6/1988 |
| JP | H05320962 A | 12/1993 |
| JP | H0633043 A | 2/1994 |
| JP | H11222687 A | 8/1999 |
| JP | H11349507 A | 12/1999 |
| JP | H11349611 A | 12/1999 |
| JP | H11349984 A | 12/1999 |
| JP | 2000-169894 A | 6/2000 |
| JP | 2000-212549 A | 8/2000 |
| JP | 2004-504370 A | 2/2004 |
| JP | 2008-188480 A | 8/2008 |
| JP | 2009-270222 A | 11/2009 |
| JP | 2010-014952 A | 1/2010 |
| JP | 2011-509334 A | 3/2011 |
| JP | 2011-219730 A | 11/2011 |
| JP | 2013-151677 A | 8/2013 |
| JP | 2014-124759 A | 7/2014 |
| JP | 2014-131872 A | 7/2014 |
| JP | 2021-042149 A | 3/2021 |

(Continued)

OTHER PUBLICATIONS

Office Action dated Jan. 9, 2023 for the corresponding Indonesian patent application No. P00202201511, with English translation.
JPO, Japanese Office Action mailed Jun. 4, 2024 for the related Japanese application No. 2020-158126, with English Machine translation, 5 pages.
JPO, Japanese Office Action mailed Jun. 4, 2024 for the related Japanese application No. 2020-158124, with English Machine translation, 5 pages.
EPO, Extended European Search Report, mailed Sep. 21, 2023, for the corresponding European patent application No. 20867374.9.
Office Action dated Apr. 25, 2024 for the related Taiwanese Application No. 109133169 and its machine English translation, 8 pages.
The State Intellectual Property Office of The People's Republic of China, "The First Office Action" dispatched Mar. 13, 2024, which was issued for the corresponding Chinese Patent Application No. 202080059993.3, with English translation, 10 pages.

(Continued)

*Primary Examiner* — Charles I Boyer
(74) *Attorney, Agent, or Firm* — LUCAS & MERCANTI, LLP

(57) ABSTRACT

A surfactant composition contains: a C12 compound of the following formula (1):

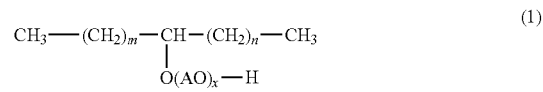

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; a C14 compound of the formula (1), where A is an alkylene group having 1 to 3 carbon atoms, x is 1 to 50, and m+n is 11; and a Y compound of the formula (1), where A is an alkylene group having 1 to 3 carbon atoms, x is 1 to 50, and m+n is at least one of 8 or less and 12 or more.

7 Claims, No Drawings

(56) References Cited

FOREIGN PATENT DOCUMENTS

| | | |
|---|---|---|
| WO | 2001/032800 A1 | 5/2001 |
| WO | 2009088778 A1 | 7/2009 |
| WO | 2012/040908 A1 | 4/2012 |

OTHER PUBLICATIONS

PCT, International Search Report for the corresponding patent application No. PCT/JP2020/035665, dated Dec. 22, 2020, with English translation.

* cited by examiner

MIXTURE OF HIGHER SECONDARY ALCOHOL ALKOXYLATES WITH DIFFERENT CARBON CHAIN LENGTHS AND METHOD FOR PRODUCING SAME

CROSS REFERENCE TO RELATED APPLICATION

This Application is a 371 of PCT/JP2020/035665 filed on Sep. 23, 2020 which, in turn, claimed the priority of Japanese Patent Application No. 2019-173623 filed on Sep. 25, 2019, Japanese Patent Application No. 2019-173624 filed on Sep. 25, 2019, and Japanese Patent Application No. 2019-173625 filed on Sep. 25, 2019, all of the above applications are incorporated herein by reference.

TECHNICAL FIELD

The present invention relates to a surfactant composition and a method for producing the surfactant composition.

BACKGROUND ART

Higher secondary alcohol ethoxylates are widely used as nonionic surfactants because they have a low pour point, and are easy to handle. As a known example, there is, for example, a detergent composition which is aimed at improving detergency and comprises a nonionic surfactant containing a higher secondary alcohol alkoxylate adduct represented by a specific chemical formula, and a primary alcohol alkoxylate, an anionic surfactant or a cationic surfactant (for example, Patent Literature 1).

CITATION LIST

Patent Literature

Patent Literature 1: JP-H11-349984 A

SUMMARY OF INVENTION

Technical Problem

On the other hand, an aqueous composition comprising a surfactant is used in a fluidized state, and therefore the extent of gelation thereof must be appropriately controlled. In addition, the present inventors have found that, in the contemporary society, there is a need for surfactant compositions which not only have basic performance such as detergency, but also meet a new challenge of reducing the odor. Accordingly, an object of the present invention is to provide a novel surfactant composition which enables improvement of detergency, does not gelate or hardly gelates, and has a reduced odor.

Means for Solving Problem

The above-described problem can be solved by the following invention.

A surfactant composition comprising: a C12 compound of the following formula (1):

[Formula 1]

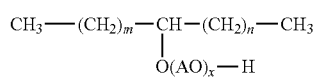
(1)

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; a C14 compound of the formula (1), where A is an alkylene group having 1 to 3 carbon atoms, x is 1 to 50, and m+n is 11; and a Y compound of the formula (1), where A is an alkylene group having 1 to 3 carbon atoms, x is 1 to 50, and m+n is at least one of 8 or less and 12 or more, wherein the content of the C12 compound is 10 to 25 mass %, the content of the C13 compound is 40 to 65 mass %, the content of the C14 compound is 20 to 49.9 mass %, and the content of the Y compound is 0.1 mass % or more and less than 5 mass %.

Advantageous Effect of the Invention

According to the present invention, it is possible to provide a novel surfactant composition which enables improvement of detergency, does not gelate or hardly gelates, and has a reduced odor.

DESCRIPTION OF EMBODIMENTS

Hereinafter, the present invention will be described. It is to be noted that the present invention is not limited to the following embodiments. Unless otherwise specified, operations and measurements of physical properties and the like are performed under the condition of room temperature (20 to 25° C.). The term "content" can be interpreted as a "content ratio" depending on context.

FIRST INVENTION

Surfactant Composition

A surfactant composition according to an aspect of the present invention comprises: a C12 compound of the following formula (1):

[Formula 2]

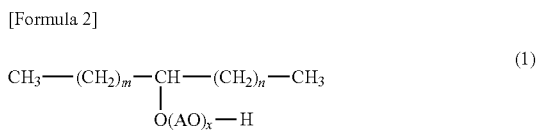
(1)

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; a C14 compound of the formula (1), where A is an alkylene group having 1 to 3 carbon atoms, x is 1 to 50, and m+n is 11; and a Y compound of the formula (1), where A is an alkylene group having 1 to 3 carbon atoms, x is 1 to 50, and m+n is at least one of 8 or less and 12 or more, wherein the content of the C12 compound is 10 to 25 mass %, the content of the C13 compound is 40 to 65 mass %, the content of the C14 compound is 20 to 49.9 mass %, and the content of the Y compound is 0.1 mass % or more and less than 5 mass %. Such a surfactant composition (sometimes referred to as a "detergent composition") enables improvement of detergency, does not gelate or hardly gelates (during handling), and has a reduced odor.

In an embodiment of the present invention, the alkylene group having 1 to 3 carbon atoms is preferably an ethylene group or a propylene group, more preferably an ethylene group. By such an embodiment, a surfactant composition having high detergency can be obtained at low cost.

In an embodiment of the present invention, x is preferably 5 to 50, more preferably 6 to 30, still more preferably 7 to 15, even more preferably 9 to 12. By such an embodiment, solubility in water and affinity to oil can be imparted to exhibit excellent detergency. The C12 compound, the C13 compound, the C14 compound and the Y compound may differ in A and x.

In an embodiment of the present invention, the content of the C12 compound is 10 mass % or more and 25 mass % or less, preferably 15 to 24 mass %, more preferably 16 to 23 mass %, still more preferably 17 to 22 mass %, even more preferably 18 to 22 mass %, even more preferably 19 to 22 mass %. By such an embodiment, both fluidity and detergency necessary for a liquid detergent can be achieved. If the content of the C12 compound is less than 10 mass %, the aqueous solution may gelate. If the content of the C12 compound is more than 25 mass %, detergency may be poor.

In an embodiment of the present invention, the content of the C13 compound is 40 to 65 mass %, preferably 45 to 65 mass %, more preferably 48 to 63 mass %, still more preferably 50 to 60 mass %, even more preferably 50 to 58 mass %, even more preferably 50 to 56 mass %, even more preferably 50 mass % or more and less than 55 mass %, and may be 51 to 53 mass. By such an embodiment, the technical effect of improving fluidity of the liquid detergent is obtained. If the content of the C13 compound is less than 40 mass %, the aqueous solution may gelate. If the content of the C13 compound is 55 mass % or more (or more than 65 mass %), the aqueous solution may gelate, or the odor level may be worsened.

In an embodiment of the present invention, the content of the C14 compound is 20 to 49.9 mass %, preferably 21 to 30 mass %, more preferably 22 to 29 mass %, still more preferably 23 to 28 mass %, even more preferably 24 to 26 mass %. By such an embodiment, the technical effect of suppressing gelation to improve detergency is obtained. If the content of the C14 compound is less than 20 mass %, detergency may be poor. If the content of the C14 compound is more than 49.9 mass %, gelation may occur.

In an embodiment of the present invention, the content of the Y compound is 0.1 mass % or more and less than 5 mass %, preferably 0.2 to 4.5 mass %, more preferably 0.4 to 4.0 mass %, and may be 0.8 to 3.8 mass %, may be 1.0 to 3.6 mass %, may be 1.2 to 3.5 mass %, or may be 1.2 mass % or more, 1.3 mass % or more, 1.4 mass % or more, 1.6 mass % or more, 1.8 mass % or more, 2.0 mass % or more, 2.2 mass % or more, 2.4 mass % or more, 2.6 mass % or more, or 2.8 mass % or more. By such an embodiment, the technical effect of suppressing gelation of a detergent to further improve detergency is obtained. If the content of the Y compound is less than 0.1 mass %, the expected effect of the present invention cannot be exhibited. If the content of the Y compound is more than 5 mass %, the odor may be worsened. As described below, the content of a C15 compound is preferably 2.0 mass % or less from the viewpoint of suppressing the odor.

According to an embodiment of the present invention, the content (content ratio) of at least one of a C9 compound, a C10 compound and a C11 compound is preferably equal to or more than the content (content ratio) of at least one of the C15 compound, a C16 compound and a C17 compound. By such an embodiment, detergency is further improved. According to an embodiment of the present invention, the ratio of the content (content ratio) of at least one of the C9 compound, the C10 compound and the C11 compound to the content (content ratio) of at least one of the C15 compound, the C16 compound and the C17 compound is 1 or more, 1.1 or more, or 1.2 or more. By such an embodiment, detergency is further improved. According to an embodiment of the present invention, the ratio of the content (content ratio) of at least one of the C9 compound, the C10 compound and the C11 compound to the content (content ratio) of at least one of the C15 compound, the C16 compound and the C17 compound is 10 or less, 7 or less, 5 or less, less than 5, 4 or less, 3 or less, 2 or less, 1.8 or less, 1.6 or less or 1.5 or less. By such an embodiment, detergency is further improved.

In an embodiment of the present invention, m+n is at least one selected from the group consisting of 7, 8, 12 and 13 in the Y compound. Specifically, when the Y compound is at least one selected from the group consisting of the C10 compound, the C11 compound, the C15 compound and the C16 compound, the technical effect of suppressing gelation of the aqueous solution to further improve detergency is obtained. The C10 compound and the C11 compound are slightly poor in detergency, but have a property of suppressing gelation and a characteristic of being excellent in ability to penetrate fibers, and the C15 compound and the C16 compound are slightly poor in property of maintaining fluidity and ability to penetrate fibers, but have a characteristic of being excellent in detergency. Accordingly, a surfactant composition having all of fluidity, penetrability and detergency can be obtained by appropriate selection from the group consisting of the C10 compound, the C11 compound, the C15 compound and the C16 compound in each application. In the present embodiment, m+n is preferably at least one selected from the group consisting of 8 and 12. Specifically, when the Y compound is at least one selected from the group consisting of the C11 compound and the C15 compound, the technical effect of achieving all of suitable fluidity, penetrability and detergency is obtained in each application as described above.

Further, since a saturated aliphatic hydrocarbon with m+n being 9, 10 or 11 as a major starting material for a surfactant containing the Y compound can further contain a saturated aliphatic hydrocarbon with m+n being 7, 8, or 13, precise distillation purification during production of saturated aliphatic hydrocarbons is unnecessary. Thus, not only equipment for performing precise distillation is unnecessary but also distillation operations can be easily performed within distillation time. Thus, productivity of saturated aliphatic hydrocarbons is improved, and as a result, the economic effect of unexpectedly reducing the production cost for the surfactant composition is also obtained.

In an embodiment of the present invention, the content of the C10 compound is 0.2 mass % or less, 0.1 mass % or less, or 0.05 mass % or less. By such an embodiment, the technical effect of improving the fluidity of a detergent is obtained.

In an embodiment of the present invention, the content of the C11 compound is 0.3 mass % or more, more than 0.3 mass %, 0.35 mass % or more, 0.4 mass % or more, 0.45 mass % or more, 0.5 mass % or more, 0.6 mass % or more, 0.7 mass % or more, 0.8 mass % or more, 0.9 mass % or more, 1.0 mass % or more, more than 1.0 mass %, 1.2 mass % or more, 1.4 mass % or more, 1.6 mass % or more, or 1.8 mass % or more. By such an embodiment, the technical effect of improving the fluidity of a detergent is obtained.

In an embodiment of the present invention, the content of the C11 compound is 3.0 mass % or less, 2.4 mass % or less, 2.2 mass % or less, 2.1 mass % or less, 2.0 mass % or less, 1.8 mass % or less, 1.6 mass % or less, 1.5 mass % or less, 1.4 mass % or less, 1.2 mass % or less, 1.0 mass % or less, 0.8 mass % or less, 0.6 mass % or less, or 0.5 mass % or less. By such an embodiment, the technical effect of suppressing deterioration of the detergency of a detergent is obtained. Thus, in an embodiment of the present invention, the content of the C11 compound is more than 0.3 mass % and 3.0 mass % or less.

In an embodiment of the present invention, the content of the C15 compound is 2.0 mass % or less, 1.9 mass % or less, 1.8 mass % or less, 1.7 mass % or less, 1.6 mass % or less, less than 1.6 mass %, 1.5 mass % or less, 1.4 mass % or less, 1.2 mass % or less, 1.0 mass % or less, or 0.05 mass % or less. By such an embodiment, the technical effect of suppressing gelation of a detergent is obtained.

Here, as shown in Examples, the presence of the C15 compound in an amount of more than 2 mass % may cause generation of an odor in the detergent composition, and therefore is not preferable. On the other hand, in an embodiment of the present invention, the content of the C15 compound is more than 0 mass %, 0.5 mass % or more, 0.6 mass % or more, 0.8 mass % or more, 1.0 mass % or more, 1.2 mass % or more, 1.4 mass % or more, 1.5 mass % or more, 1.6 mass % or more, more than 1.6 mass %, or 1.8 mass % or more. By such an embodiment, the technical effect of improving the detergency of a detergent is obtained.

In an embodiment of the present invention, the content of the C11 compound with m+n being 8 is more than 0.3 mass % (0.6 mass % or more, 0.7 mass % or more, 0.8 mass % or more, or 0.9 mass % or more) and 3.0 mass % or less, and the content of the C15 compound with m+n being 12 is less than 1.6 mass %. By such an embodiment, the technical effect of being very excellent in fluidity, penetrability and detergency as a detergent is obtained.

In an embodiment of the present invention, the total of the content of the C12 compound, the content of the C13 compound, the content of the C14 compound and the content of the Y compound is 100 mass %.

While various upper limits, lower limits and ranges of contents (content ratios) are disclosed herein, it should be appreciated that all the upper limits, lower limits, ranges or combinations thereof are disclosed herein. That is, they warrant the legality of amendments.

Method for Producing Surfactant Composition

In an embodiment of the present invention, a method for producing a surfactant composition comprises adding an alkylene oxide to a secondary alcohol mixture containing: 10 to 25 mass % of a C12 precursor of the following formula (2):

[Formula 3]

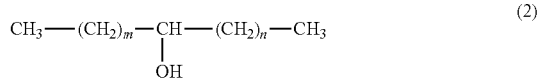

(2)

where m+n is 9; 40 to 65 mass % of a C13 precursor of the formula (2), where m+n is 10; 20 to 49.9 mass % of a C14 precursor of the formula (2), where m+n is 11; and 0.1 mass % or more and less than 5 mass % of a Y precursor of the formula (2), where m+n is at least one of 8 or less and 12 or more. According to such a production method, it is possible to prepare a surfactant composition which improves detergency and does not gelate or hardly gelates during handling.

Preparation of Secondary Alcohol Mixture

In an embodiment of the present invention, the secondary alcohol mixture of the formula (2) can be obtained by carrying out an oxidation step of oxidizing a saturated aliphatic hydrocarbon mixture as starting materials, and an alcoholization step.

In an embodiment of the present invention, the oxidation step can be carried out by referring to or combining heretofore known findings. It is possible to appropriately refer to or combine descriptions concerning the oxidation step in, for example, JP-S48-34807 A and "Oil Chemistry", 24, 7, p.p. 427-434 (1975), but the method for carrying out the oxidation step is not limited thereto. An exemplary method will be now described. A saturated aliphatic hydrocarbon mixture as starting materials is subjected to an oxidation reaction by injecting a gas containing oxygen and nitrogen in the presence of a boron compound. As the boron compound, metaboric acid, orthoboric acid or the like is suitable. Subsequently, an alcohol prepared through hydrolysis by hot-water treatment or the like is esterified with orthoboric acid. Preferably, the alcohol is reacted with boric acid under the conditions of 10 to 300 hPa and 150 to 190° C. to perform the esterification with orthoboric acid. By subjecting the mixture containing an orthoboric acid ester to flash distillation preferably at 1 to 100 hPa, unreacted saturated aliphatic hydrocarbons can be removed. Subsequently, a hydrolysis step of hydrolyzing residues on distillation to separate the residues into boric acid and an organic acid layer is carried out, followed by performing saponification in which the separated organic layer is saponified with an alkali to be separated into an alkali aqueous solution layer and a crude alcohol layer. In addition, water washing is performed to remove organic acids and organic acid esters. Thereafter, fractional distillation is performed to obtain a secondary alcohol mixture.

Thus, in an embodiment of the present invention, the oxidation step includes subjecting a saturated aliphatic hydrocarbon mixture as starting materials for the present invention to an oxidation reaction by adding a gas containing oxygen and nitrogen in the presence of a boron compound. An embodiment of the present invention includes preparing a mixture containing an orthoboric acid ester by esterifying an alcohol, which is formed by the oxidation reaction, with orthoboric acid. An embodiment of the present invention includes distilling the mixture containing an orthoboric acid ester to remove unreacted saturated aliphatic hydrocarbons. In an embodiment of the present invention, a hydrolysis step of hydrolyzing resides on distillation to separate the residues into boric acid and an organic layer is carried out. An embodiment of the present invention includes subjecting the separated organic layer to saponification with an alkali, more specifically saponification for separation into an alkali aqueous solution layer and a crude alcohol layer, and also performing water washing. An embodiment of the present invention includes removing organic acids and organic acid esters, and then performing fractional distillation to obtain a secondary alcohol mixture.

Saturated Aliphatic Hydrocarbon Mixture as Starting Materials

Here, the saturated aliphatic hydrocarbon mixture as starting materials serves as starting materials for obtaining a secondary alcohol mixture of the formula (2). In an embodiment of the present invention, the saturated aliphatic hydrocarbon mixture as starting materials contains a saturated aliphatic hydrocarbon having 12 carbon atoms (corresponding to the C12 compound), a saturated aliphatic hydrocarbon having 13 carbon atoms (corresponding to the C13 compound), a saturated aliphatic hydrocarbon having 14 carbon atoms (corresponding to the C14 compound), and saturated aliphatic hydrocarbons having or less carbon atoms and 15 or more carbon atoms (corresponding to the Y compound), at a predetermined ratio.

Specifically, the saturated aliphatic hydrocarbon mixture as starting materials contains 10 to 25 mass % of a saturated aliphatic hydrocarbon having 12 carbon atoms, 40 to 65 mass % of a saturated aliphatic hydrocarbon having 13 carbon atoms, 20 to 49.9 mass % of a saturated aliphatic hydrocarbon having 14 carbon atoms, and 0.1 mass % or more and less than 5 mass % of saturated aliphatic hydrocarbons having 11 or less carbon atoms and 15 or more carbon atoms. Descriptions of the preferred contents (content ratios (mass %)) of the saturated aliphatic hydrocarbons having the respective numbers of carbons, and the ranges, upper limits and lower limits thereof in the saturated aliphatic hydrocarbon mixture as starting materials are omitted here because descriptions given in the section <Surfactant Composition>above are also applied thereto. More specifically, the description of the C12 compound can be applied to the description of the saturated aliphatic hydrocarbon having 12 carbon atoms, the description of the C13 compound can be applied to the description of the saturated aliphatic hydrocarbon having 13 carbon atoms, the description of the C14 compound can be applied to the description of the saturated aliphatic hydrocarbon having 14 carbon atoms, and the description of the Y compound can be applied to the description of the saturated aliphatic hydrocarbons having 11 or less carbon atoms and 15 or more carbon atoms, mutatis mutandis.

As a specific example, the above recitation "In an embodiment of the present invention, the content of the Y compound is 0.1 mass % or more and less than 5 mass %, preferably 0.2 to 4.5 mass %, more preferably 0.4 to 4.0 mass %, and may be 0.8 to 3.8 mass %, may be 1.0 to 3.6 mass %, may be 1.2 to 3.5 mass %, or may be 1.2 mass % or more, 1.3 mass % or more, 1.4 mass % or more, 1.6 mass % or more, 1.8 mass % or more, 2.0 mass % or more, 2.2 mass % or more, 2.4 mass % or more, 2.6 mass % or more, or 2.8 mass % or more" can be read to mean that "in an embodiment of the present invention, the content of the saturated aliphatic hydrocarbons having 11 or less carbon atoms and 15 or more carbon atoms is 0.1 mass % or more and less than 5 mass %, preferably 0.2 to 4.5 mass %, more preferably 0.4 to 4.0 mass %, and may be 0.8 to 3.8 mass %, may be 1.0 to 3.6 mass %, may be 1.2 to 3.5 mass %, or may be 1.2 mass % or more, 1.3 mass % or more, 1.4 mass % or more, 1.6 mass % or more, 1.8 mass % or more, 2.0 mass % or more, 2.2 mass % or more, 2.4 mass % or more, 2.6 mass % or more, or 2.8 mass % or more, in the saturated aliphatic hydrocarbon mixture as starting materials".

In an embodiment of the present invention, the preparation of a saturated aliphatic hydrocarbon mixture as starting materials containing the saturated aliphatic hydrocarbon having 12 carbon atoms, the saturated aliphatic hydrocarbon having 13 carbon atoms, the saturated aliphatic hydrocarbon having 14 carbon atoms and the saturated aliphatic hydrocarbons having 11 or less carbon atoms and 15 or more carbon atoms, at a predetermined ratio can also be performed by referring to or combining heretofore known findings, for example by carrying out operations for separation by a conventional method (e.g. distillation), and the like.

According to an embodiment of the present invention, the secondary alcohol mixture, to which an alkylene oxide is to be added, is prepared by subjecting a saturated aliphatic hydrocarbon mixture as starting materials to an oxidation step, etc., and the saturated aliphatic hydrocarbon mixture as starting materials contains 10 to 25 mass % of a saturated aliphatic hydrocarbon having 12 carbon atoms, 40 to 65 mass % of a saturated aliphatic hydrocarbon having 13 carbon atoms, 20 to 49.9 mass % of a saturated aliphatic hydrocarbon having 14 carbon atoms and 0.1 mass % or more and less than 5 mass % of saturated aliphatic hydrocarbons having 11 or less carbon atoms and 15 or more carbon atoms. By adding an alkylene oxide to the thus-prepared secondary alcohol mixture, a surfactant composition can be produced.

Addition of Alkylene Oxide

In an embodiment of the present invention, a method for producing a surfactant composition comprises adding an alkylene oxide to a secondary alcohol mixture which is prepared by, for example, the above-described method and contains: 10 to 25 mass % of a C12 precursor of the following formula (2):

[Formula 4]

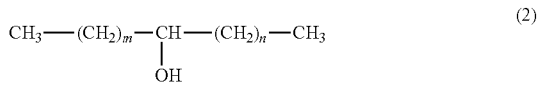

(2)

where m+n is 9; 40 to 65 mass % of a C13 precursor of the formula (2), where m+n is 10; 20 to 49.9 mass % of a C14 precursor of the formula (2), where m+n is 11; and 0.1 mass % or more and less than 5 mass % of a Y precursor of the formula (2), where m+n is at least one of 8 or less and 12 or more. According to such a production method, it is possible to prepare a surfactant composition which improves detergency and does not gelate or hardly gelates during handling.

Descriptions of the preferred contents (content ratios (mass %)) of the precursors, and the ranges, upper limits and lower limits thereof in the secondary alcohol mixture are omitted here because descriptions given in the section <Surfactant Composition>above are also applied thereto. More specifically, the description of the C12 compound can be applied to the description of the C12 precursor, the description of the C13 compound can be applied to the description of the C13 precursor, the description of the C14 compound can be applied to the description of the C14 precursor, and the description of the Y precursor can be applied to the description of the Y compound, mutatis mutandis. More specifically, they can be applied by reading the saturated aliphatic hydrocarbon mixture as starting materials as the secondary alcohol mixture in the specific examples described in [Saturated aliphatic hydrocarbon mixture as starting materials].

In an embodiment of the present invention, the addition of an alkylene oxide can be performed by referring to or combining heretofore known findings. Heretofore known examples include methods described in, for example, JP-2003-221593 A, JP-S48-34807 and "Oil Chemistry", 24, 7, p.p. 427-434 (1975). The addition of an alkylene oxide will now be described by giving specific examples, but is not limited thereto.

In an embodiment of the present invention, ethylene oxide, propylene oxide or the like is suitable as an alkylene oxide. In an embodiment of the present invention, nitrogen purge is performed before an alkylene oxide is added. The initial nitrogen pressure in nitrogen purge is preferably 0.05 to 1.0 MPa, more preferably 0.05 to 0.4 MPa. In an embodiment of the present invention, the reaction temperature is preferably 40 to 100° C., and more preferably 40 to 70° C. In an embodiment of the present invention, the number of moles of an alkylene oxide fed per 1 mole of hydroxyl groups in the secondary alcohol mixture is preferably 1 to 5, more preferably 2 to 4. The catalyst is preferably an acid catalyst such as boron trifluoride or tris(pentafluorophenyl)borane. By washing the resulting oil layer with an aqueous solution of sodium hydroxide, potassium hydroxide or the like after the reaction, the catalyst and by-produces can be removed to obtain an alkylene oxide adduct. It is preferable to remove an unreacted alcohol by performing distillation for further enhancing the purity. By adding an alkali compound such as sodium hydroxide or potassium hydroxide to the resulting alkylene oxide adduct, and performing an addition reaction with the alkylene oxide again, an alkylene oxide adduct suitable for use in a detergent composition can be obtained. The average number of moles of the alkylene oxide added is preferably 5 to 50, more preferably 6 to 30, still more preferably 7 to 15, even more preferably 9 to 12, per 1 mole of hydroxyl groups.

Applications of Surfactant Composition

In an embodiment of the present invention, with regard to applications of the surfactant composition, use as a detergent is desirable because the surfactant composition of the present invention does not gelate or hardly gelates, is excellent in detergency, and has a reduced odor.

In an embodiment of the present invention, the surfactant composition may be used alone, or heretofore known other surfactants may be used in combination. Examples of such surfactants include anionic surfactants such as alkylbenzene sulfonic acid salts, alkyl sulfuric acid ester salts, α-olefin sulfonic acid salts, alkyl sulfonic acid salts, aliphatic amidosulfonic acid salts, dialkyl sulfosuccinic acid salts and alkyl ether sulfuric ester salts, cationic surfactants such as alkylamine salts and quaternary ammonium salts, and amphoteric surfactants such as alkylbetaines.

In an embodiment of the present invention, various additives can be added to the surfactant composition. Examples of such additives include alkaline agents, builders, perfumes, fluorescent bleaching agents, coloring agents, foaming agents, foam stabilizers, polishing agents, bactericides, bleaching agents, enzymes, antiseptic agents, dyes and solvents.

In an embodiment of the present invention, when used as a detergent, the surfactant composition can be effectively used as detergents for clothes, fiber products, eating utensils, containers, miscellaneous goods and fixings, food products, building maintenance products, dwelling houses, furniture, automobiles, aircrafts and metallic products, shampoo, body shampoo and the like.

In an embodiment of the present invention, the surfactant composition may be used as an emulsifier. Regarding oily substances for which the emulsifier can be used, there is no particular limitation, and mineral oil, animal and vegetable oils and synthetic oil can be used. One of these substances can be used alone, or two or more thereof can be mixed and used. Examples of the mineral oil include spindle oil, machine oil and liquid paraffin oil. Examples of the animal and vegetable oils include beef fat, pork fat, fish oil, whale oil, rape seed oil, sesame oil, coconut oil, soybean oil, palm oil, camellia oil and castor oil. In an embodiment of the present invention, the emulsifier can be used for agricultural chemicals, metalworking oil, paints, emulsifiers for emulsion polymerization, and the like.

EXAMPLES

Hereinafter, the present invention will be described in more detail by way of Examples and Comparative Examples. However, the present invention should not be understood only on the basis of these Examples and Comparative Examples, and Examples obtained by appropriately combining technical means disclosed in Examples are also within the scope of the present invention.

Example 1

Oxidation Step and Alcoholization Step 1000 g of a mixture of saturated aliphatic hydrocarbons having a carbon number distribution as shown in Table 1 below, and 25 g of metaboric acid were put in a 3 L-volume cylindrical reactor, and subjected to an oxidation reaction at 170° C. at ordinary pressure for 2 hours by injecting a gas having an oxygen concentration of 3.5 vol % and a nitrogen concentration of 96.5 vol % at a rate of 430 L per hour.

50 mass % of the oxidation reaction mixed liquid was hydrolyzed with a large amount of hot water (95° C.), and an oil layer containing the formed alcohol was separated. The remaining 50% of the oxidation reaction liquid was mixed with this oil layer to make an adjustment so that 1.04 equivalents of the boric acid ester compound in terms of an orthoboric acid ester was present. The resulting mixture was treated at 200 hPa and 170° C. to esterify the alcohol contained therein with orthoboric acid. The mixture containing an orthoboric acid ester was subjected to flash distillation at 7 hPa to remove unreacted saturated aliphatic hydrocarbons until the temperature of the residual liquid was 170° C. Subsequently, the residual liquid was hydrolyzed with a large amount of hot water at 95° C. to remove the boric acid to the aqueous phase. The resulting oil layer was saponified, and washed with water to remove organic acids and organic acid esters. This oil phase was subjected to fractional distillation at 7 hPa. The fraction having a boiling point in the range of 95° C. or higher and lower than 120° C. as the first fraction was a mixture of a small amount of paraffin, a carbonyl compound and a monohydric primary alcohol. The second fraction (a fraction having a boiling point in the range of 120 to 150° C.) consisted mostly of a monohydric secondary alcohol while including a very small amount of a carbonyl compound and a polyhydric secondary alcohol. As this second fraction, a monohydric secondary alcohol was obtained. In the manner described above, a secondary alcohol mixture was obtained.

Alkylene Oxide Adding Step

In a SUS 3 L autoclave with a stirrer, thermometer and an inlet tube for introducing ethylene oxide (EO), 1 kg of the secondary alcohol mixture obtained as described above was placed, and nitrogen purge was performed. Thereafter, 1.68 g of a $BF_3$-Et catalyst ($BF_3$: 46 to 49%) was placed in the autoclave, and ethylene oxide (EO) was fed in an amount of 1.7 moles per 1 mole of hydroxyl groups at 55±5° C. at an initial nitrogen pressure of 0.05 MPa to add the ethylene oxide. Thereafter, the reaction liquid was washed at 90° C. by adding a NaOH solution, and washed with water to a pH of 7 or less. Subsequently, the oil phase was placed in a 3 L three-necked glass flask, a distillation tower (filling material:

Packing Dixon with an inner diameter of 40 mm, a length of 200 mm and a theoretical stage number of 3) was attached, and distillation was performed to obtain an ethoxylate adduct in an amount of 3 moles per 1 mole of hydroxyl groups in terms of an average number of moles added. In the same type of autoclave as described above, 558 g of the resulting ethoxylate adduct and 1 g of potassium hydroxide were placed, and nitrogen purge was performed. The pressure inside the reactor was then set to 15 kPa with nitrogen, and the mixture was heated at 150° C. to react 442 g of ethylene oxide. After the reaction, the reaction product was neutralized with acetic acid to obtain a surfactant which is an ethylene oxide adduct. It was confirmed that the resulting surfactant composition was represented by the formula (1), and that the contents of a C11 compound with m+n being 8 (i.e. a Y compound), a C12 compound with m+n being 9, a C13 compound with m+n being 10, a C14 compound with m+n being 11 and a C15 compound with m+n being 12 (i.e. a Y compound) (hereinafter, referred to as a carbon number distribution) were as shown in Table 1. The average number of moles of EO added was found to be 9.0 by the following method for measuring a hydroxyl value.

Examples 2, 3, 4 and 5 and Comparative Examples 1 to 4

Surfactant compositions which were ethoxylate adducts were obtained in the same manner as in Example 1 except that the mixture of saturated aliphatic hydrocarbons in Example 1 was changed as shown in Table 1 below. It was confirmed that the resulting surfactant compositions were each represented by the formula (1), and that the carbon number distributions of the surfactant compositions of Examples 2 to 5 and Comparative Examples 1 to 4 were as shown in Table 1. The average numbers of moles of EO added were found to be 9.0, 9.0, 9.0, 9.0, 9.0, 8.6, 9.4 and 9.0, respectively, by the following method for measuring a hydroxyl value.

The carbon number distribution in the starting material paraffin (mixture of saturated aliphatic hydrocarbons), the carbon number distribution in the secondary alcohol (mixture of secondary alcohols) and the carbon number distribution in the alkoxylate (ethoxylate adduct) are the same.

Evaluation Method

Method for Measuring Hydroxyl Value 444 g of phthalic anhydride of a special grade reagent was taken, and dissolved in pyridine of a special grade reagent to prepare a total volume of 3 L of a phthalation reagent. About 1 g of a sample was precisely weighed and taken in a Teflon flask, 9 mL of the phthalation reagent was added, and the flask was capped with a Teflon lid. Here, a flask having no sample was used as a blank test. The flask was placed on a hot plate whose surface temperature was adjusted to 120° C., and the sample was heated for 90 minutes. During heating, the flask was lightly shaken every 15 minutes to stir the sample. After the heating, 15 mL of pure water was added, the resulting mixture was allowed to cool for 10 minutes, 50 mL of pure water was then added, and the resulting mixture was lightly stirred. The flask was set in an automatic titrator (AT-610 manufactured by KYOTO ELECTRONICS INDUSTRY CO., LTD.), and neutralization titration was performed with a 0.5 mol/L potassium hydroxide solution (titration solution for volumetric analysis manufactured by KANTO KAGAKU). Measurement was performed in triplicate per sample, and the hydroxyl value was calculated from the following equation.

$$HV=\{(VB-VS) \times N \times F \times 56.11\}/S$$

HV: hydroxyl value (mg KOH/g)
VB: titer with 0.5 mol/L aqueous potassium hydroxide solution in blank test (mL)
VS: titer with 0.5 mol/L aqueous potassium hydroxide solution for sample (mL)
N: 0.5 (concentration of aqueous potassium hydroxide solution (mol/L))
F: factor of aqueous potassium hydroxide solution at 0.5 mol/L
S: amount of sample collected (g)

From the resulting hydroxyl value, the average molecular weight was calculated, and from a difference between this average molecular weight and the average molecular weight of the secondary alcohol, the average number of moles of EO added was calculated.

$$n=(56110/HV-Mw)/44.05$$

Mw: average molecular weight of secondary alcohol

Method for Measuring Carbon Number Distribution in Saturated Aliphatic Hydrocarbon The carbon number distribution in the saturated aliphatic hydrocarbon was measured under the following conditions by using the following apparatus.
Apparatus: GC-2010 (SHIMADZU)
Conditions: column: UA1 (MS/HT)-30M-0.25F (GL Science)
Injection amount: 0.5 ml
Injection method: splitless
Injection temperature: 400° C.
Column temperature: 50° C. (10 min) to 5° C./min-400° C. (30 min)
Carrier gas: He, 1 ml/min
Detector: FID (400° C., $H_2$ 50 ml/min, Air 400 ml/min, $N_2$ 20 ml/min)

Method for Measuring Carbon Number Distribution in Surfactant Composition

Apparatus: Alliance 2695 HPLC (Waters)
Column: Intersil ODS-2 having an inner diameter of 3.0 mm and a length of 150 mm (GL Science)
Column temperature: 40° C.
Injection amount: 100 μl
Sample concentration: 2%
Eluent: acetonitrile/water=65/35 (vol %)
Flow rate: 1 ml/min
Detector: RI

HLB

HLBs of the surfactant compositions of Examples and Comparative Examples are shown in Table 1. The HLBs are values determined by the Griffin method. According to an embodiment of the present invention, the HLB of the surfactant composition is preferably 10.0 to 16.0, more preferably 11.0 to 15.0, and still more preferably 12.0 to 14.0.

(1) Extent of Gelation

An aqueous solution of a surfactant composition (25° C.) was prepared at a predetermined concentration (40 mass % to 50 mass %) as shown in Table 1. Thereafter, the aqueous solution was heated to 40° C. over 60 minutes. Thereafter, the aqueous solution was naturally cooled to 25° C. in an environment at a room temperature of 25° C., and whether or not the aqueous solution had fluidity was visually examined.

Thus, according to an embodiment of the present invention, the extent of gelation is determined on a 40 mass % to 50 mass % aqueous solution of surfactant composition (25° C.)

(2) Detergency

A test on detergency was conducted under the following conditions by referring to JIS K-3362: 2008. Specifically, first, a contaminant was prepared. The contaminant has the composition of oleic acid: 28.3 mass %, triolein: 15.6 mass %, cholesterol oleate: 12.2 mass %, liquid paraffin: 2.5 mass %, squalene: 2.5 mass %, cholesterol: 1.6 mass %, gelatin: 7.0 mass %, red-yellow soil: 29.8 mass % and carbon black: 0.5 mass %.

This contaminant was applied to a cloth (5 cm×5 cm) to prepare a contaminated cloth. Five contaminated cloths were prepared in the same manner. Thus, a total of six contaminated cloths were prepared.

The total of six contaminated cloths and 30 g of cotton were immersed in 900 g of water (30° C.) containing Ca at 1.5 mmol/L and Mg at 1.0 mmol/L. A surfactant composition was added to the water (30° C.) to a concentration of 0.05 wt %. Thereafter, washing was performed at a stirring rate of 120 rpm for 20 minutes.

Before and after the washing, the reflectance of the contaminated cloth was measured at four points (two points on each of the front and the back) for each test cloth, and from the average value thereof (a total of 24 points), the difference in reflectance between before and after the washing ($\Delta Z$) was evaluated. The reflectance was measured by using a color-difference meter (Spectral Color-Difference Meter SA 5500 (manufactured by DENSHOKU INDUSTRIES Co., Ltd.)).

Conditions

Measurement diameter: 28 mm
Light source for observation: D65
Conditions for observation: visual field at 10 degrees
Measurement item: Z (3) Odor Whether or not a surfactant had an odor was examined by the following sensory test. The surfactant composition obtained in each of Examples and Comparative Examples was taken in a 50 ml glass container, and heated in a hot-water bath at 50° C. for 30 minutes, and five persons then determined whether or not there was an odor. The surfactant composition was rated × when the number of persons smelling an odor was 2 or more, and the surfactant composition was rated ○ when the number of persons smelling an odor was 1 or less.

TABLE 1

|  | Carbon number distribution in mixture of saturated aliphatic hydrocarbons (mass %) | EO | HLB | Evaluation (1) Extent of gelation | | | | Evaluation (2) Detergency | | Evaluation (3) Odor | Overall evaluation |
|---|---|---|---|---|---|---|---|---|---|---|---|
|  |  |  |  | 40% | 45% | 50% | Evaluation | $\Delta Z(\%)$ | Evaluation | Evaluation |  |
| Example 1 | C11/12/13/14/15 = 0.5/20/54.4/25/0.1 | 9.0 mol | 13.3 | Liquid | Liquid | Liquid | ○ | 27.6 | ○ | ○ | ○ |
| Example 2 | C11/12/13/14/15 = 1/20/53/25/1 | 9.0 mol | 13.3 | Liquid | Liquid | Liquid | ○ | 28.0 | ○ | ○ | ○ |
| Example 3 | C11/12/13/14/15 = 2/20/51.5/25/1.5 | 9.0 mol | 13.3 | Liquid | Liquid | Liquid | ○ | 28.2 | ○ | ○ | ○ |
| Example 4 | C11/12/13/14/15 = 0.3/20/53.1/25/1.6 | 9.0 mol | 13.3 | Liquid | Liquid | Liquid | ○ | 27.2 | ○ | ○ | ○ |
| Example 5 | C11/12/13/14/15 = 0.4/21.4/52.5/25.7/0 | 9.0 mol | 13.3 | Liquid | Liquid | Liquid | ○ | 27.6 | ○ | ○ | ○ |
| Comparative Example 1 | C11/12/13/14/15 = 0/20/55/25/0 | 9.0 mol | 13.3 | Liquid | Gel | Liquid | X | 27.4 | ○ | ○ | X |
| Comparative Example 2 | C11/12/13/14/15 = 0/70/20/10/0 | 8.6 mol | 13.3 | Liquid | Liquid | Liquid | ○ | 25.1 | X | ○ | X |
| Comparative Example 3 | C11/12/13/14/15 = 0/10/20/70/0 | 9.4 mol | 13.3 | Gel | Gel | Gel | X | 31.4 | ◉ | ○ | X |
| Comparative Example 4 | C11/12/13/14/15 = 2.5/20/50.0/25/2.5 | 9.0 mol | 13.3 | Liquid | Liquid | Liquid | ○ | 28.6 | ○ | X | X |

SECOND INVENTION

Subsequently, the second invention will be described.
[Title of Invention] SURFACTANT COMPOSITION AND METHOD FOR
PRODUCING SAME

TECHNICAL FIELD

The present invention relates to a surfactant composition, and a method for producing the surfactant composition.

BACKGROUND ART

Higher secondary alcohol ethoxylates are widely used as nonionic surfactants because they have a low pour point, and are easy to handle. As a known example, there is, for example, a detergent composition which is aimed at improving detergency and comprises a nonionic surfactant containing a higher secondary alcohol alkoxylate adduct represented by a specific chemical formula, and a primary alcohol alkoxylate, an anionic surfactant or a cationic surfactant (for example, Patent Literature 1).

CITATION LIST

Patent Literature

[Patent Literature 1] JP-H11-349984 A

SUMMARY OF INVENTION

Technical Problem

A surfactant basically has three major actions: the penetrating effect, the emulsifying effect and the dispersing effect, and these actions are integrally exerted to remove dirt on objects to be washed, such as fibers and eating utensils. Among them, the penetrating effect is the effect of allowing water to penetrate between dirt and an object to be washed, and a higher penetrating effect enables removal of dirt at a deeper portion of an object to be washed. Further, when the surfactant has a good foam breaking property, rinsing can be performed quickly, leading to reduction of washing operation time.

Accordingly, an object of the present invention is to provide a novel surfactant composition having a high penetrating effect and a good foam breaking property.

Means for Solving Problem

The above-described problem can be solved by the following invention.

A surfactant composition comprising: a C12 compound of the following formula (1):

[Formula 1]

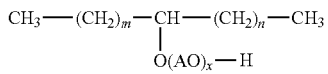

(1)

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is more than 25 mass % and 100 mass % or less, the content of the C13 compound is 0 to 40 mass %, and the content of the C14 compound is 0 to 20 mass %.

Advantageous Effect of the Invention

According to the present invention, it is possible to provide a novel surfactant composition having a high penetrating effect and a good foam breaking property.

DESCRIPTION OF EMBODIMENTS

Hereinafter, the present invention will be described. It is to be noted that the present invention is not limited to the following embodiments. Unless otherwise specified, operations and measurements of physical properties and the like are performed under the condition of room temperature (20 to 25° C.). The term "content" can be interpreted as a "content ratio" depending on context.

Surfactant Composition

A surfactant composition according to an aspect of the present invention is a surfactant composition comprising: a C12 compound of the following formula (1):

[Formula 2]

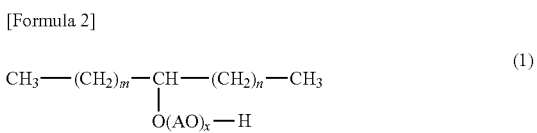

(1)

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is more than 25 mass % and 100 mass % or less, the content of the C13 compound is 0 to 40 mass %, and the content of the C14 compound is 0 to 20 mass %. Such a surfactant composition (sometimes referred to as a "detergent composition") is a novel detergent composition having a high penetrating effect and a good foam breaking property.

In an embodiment of the present invention, the alkylene group having 1 to 3 carbon atoms is preferably an ethylene group or a propylene group, more preferably an ethylene group. By such an embodiment, a surfactant composition having high detergency can be obtained at low cost.

In an embodiment of the present invention, x is preferably 5 to 50, more preferably 6 to 30, still more preferably 7 to 15, even more preferably 9 to 12. By such an embodiment, solubility in water and affinity to oil can be imparted to exhibit excellent detergency. The C12 compound, the C13 compound and the C14 compound may differ in A and x.

In an embodiment of the present invention, the content of the C12 compound is more than 25 mass % and 100 mass % or less. If the content of the C12 compound is 25 mass % or less, expected effects of the present invention may not be exhibited. In an embodiment of the present invention, the content of the C12 compound is preferably 30 mass % or more, 40 mass % or more, 50 mass % or more, 60 mass % or more, or 65 mass % or more. By such an embodiment, excellent penetrability can be exhibited. In an embodiment of the present invention, the content of the C12 compound is less than 100 mass %, 90 mass % or less, 80 mass % or less, or 75 mass % or less. By such an embodiment, at least one of the effects of improving penetrability, improving the foam breaking property and improving fluidity of the liquid detergent is obtained.

In an embodiment of the present invention, the content of the C13 compound is 0 to 40 mass %. If the content of the C13 compound is more than 40 mass %, the expected effects of the present invention may not be exhibited. In an embodiment of the present invention, the content of the C13 compound is more preferably more than 0 mass %, 5 mass % or more, 10 mass % or more, 15 mass % or more, or 18 mass % or more. By such an embodiment, fluidity of the liquid detergent can be improved. In an embodiment of the present invention, the content of the C13 compound is preferably 35 mass % or less, 30 mass % or less, 25 mass % or less, or 23 mass % or less. By such an embodiment, at least one of the effects of improving penetrability, improving the foam breaking property and improving fluidity of the liquid detergent is obtained.

In an embodiment of the present invention, the content of the C14 compound is 0 to 20 mass %. If the content of the C14 compound is more than 20 mass %, expected effects of the present invention may not be exhibited. In an embodiment of the present invention, the content of the C14 compound is preferably more than 0 mass %, 2 mass % or more, 4 mass % or more, 6 mass % or more, or 8 mass % or more. By such an embodiment, excellent detergency can be exhibited. In an embodiment of the present invention, the content of the C14 compound is preferably 18 mass % or less, 16 mass % or less, 14 mass % or less, or 12 mass % or less. By such an embodiment, excellent penetrability can be exhibited.

In an embodiment of the present invention, the total of the content of the C12 compound, the content of the C13 compound and the content of the C14 compound is 100 mass %.

While various upper limits, lower limits and ranges of contents (content ratios) are disclosed herein, it should be appreciated that all the upper limits, lower limits, ranges or combinations thereof are disclosed herein. That is, they warrant the legality of amendments.

Method for Producing Surfactant Composition

In an embodiment of the present invention, a method for producing a surfactant composition comprises adding an alkylene oxide to a secondary alcohol mixture containing: more than 25 mass % and 100 mass % or less of a C12 precursor of the following formula (2):

[Formula 3]

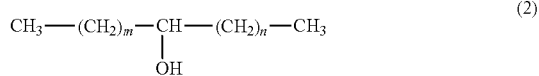

(2)

where m+n is 9; 0 to 40 mass % of a C13 precursor of the formula (2), where m+n is 10; and 0 to 20 mass % of a C14 precursor of the formula (2), where m+n is 11. According to such a production method, it is possible to produce a surfactant composition having a high penetrating effect and a good foam breaking property.

Preparation of Secondary Alcohol Mixture

In an embodiment of the present invention, the secondary alcohol mixture of the formula (2) can be obtained by carrying out an oxidation step of oxidizing a saturated aliphatic hydrocarbon mixture as starting materials, and an alcoholization step.

In an embodiment of the present invention, the oxidation step can be carried out by referring to or combining heretofore known findings. It is possible to appropriately refer to or combine descriptions concerning the oxidation step in, for example, JP-S48-34807 A and "Oil Chemistry", 24, 7, p.p. 427-434 (1975), but the method for carrying out the oxidation step is not limited thereto. An exemplary method will be now described. A saturated aliphatic hydrocarbon mixture as starting materials is subjected to an oxidation reaction by injecting a gas containing oxygen and nitrogen in the presence of a boron compound. As the boron compound, metaboric acid, orthoboric acid or the like is suitable. Subsequently, an alcohol prepared through hydrolysis by hot-water treatment or the like is esterified with orthoboric acid. Preferably, the alcohol is reacted with boric acid under the conditions of 10 to 300 hPa and 150 to 190° C. to perform the esterification with orthoboric acid. By subjecting the mixture containing an orthoboric acid ester to flash distillation preferably at 1 to 100 hPa, unreacted saturated aliphatic hydrocarbons can be removed. Subsequently, a hydrolysis step of hydrolyzing residues on distillation to separate the residues into boric acid and an organic acid layer is carried out, followed by performing saponification in which the separated organic layer is saponified with an alkali to be separated into an alkali aqueous solution layer and a crude alcohol layer. In addition, water washing is performed to remove organic acids and organic acid esters. Thereafter, fractional distillation is performed to obtain a secondary alcohol mixture.

Thus, in an embodiment of the present invention, the oxidation step includes subjecting a saturated aliphatic hydrocarbon mixture as starting materials for the present invention to an oxidation reaction by adding a gas containing oxygen and nitrogen in the presence of a boron compound. An embodiment of the present invention includes preparing a mixture containing an orthoboric acid ester by esterifying an alcohol, which is formed by the oxidation reaction, with orthoboric acid. An embodiment of the present invention includes distilling the mixture containing an orthoboric acid ester to remove unreacted saturated aliphatic hydrocarbons. In an embodiment of the present invention, a hydrolysis step of hydrolyzing resides on distillation to separate the residues into boric acid and an organic layer is carried out. An embodiment of the present invention includes subjecting the separated organic layer to saponification with an alkali, more specifically saponification for separation into an alkali aqueous solution layer and a crude alcohol layer, and also performing water washing. An embodiment of the present invention includes removing organic acids and organic acid esters, and then performing fractional distillation to obtain a secondary alcohol mixture.

Saturated Aliphatic Hydrocarbon Mixture as starting Materials

Here, the saturated aliphatic hydrocarbon mixture as starting materials serves as starting materials for obtaining a secondary alcohol mixture of the formula (2). In an embodiment of the present invention, the saturated aliphatic hydrocarbon mixture as starting materials contains a saturated aliphatic hydrocarbon having 12 carbon atoms, a saturated aliphatic hydrocarbon having 13 carbon atoms and a saturated aliphatic hydrocarbon having 14 carbon atoms, at a predetermined ratio.

Specifically, the saturated aliphatic hydrocarbon mixture as starting materials contains more than 25 mass % and 100 mass % or less of a saturated aliphatic hydrocarbon having 12 carbon atoms (which corresponds to the C12 compound), 0 to 40 mass % of a saturated aliphatic hydrocarbon having 13 carbon atoms (which corresponds to the C13 compound), and 0 to 20 mass % of a saturated aliphatic hydrocarbon having 14 carbon atoms (which corresponds to the C14 compound). Descriptions of the preferred contents (content ratios (mass %)) of the saturated aliphatic hydrocarbons having the respective numbers of carbons, and the ranges, upper limits and lower limits thereof in the saturated aliphatic hydrocarbon mixture as starting materials are omitted here because descriptions given in the section <Surfactant Composition>above are also applied thereto. More specifically, the description of the C12 compound can be applied to the description of the saturated aliphatic hydrocarbon having 12 carbon atoms, the description of the C13 compound can be applied to the description of the saturated aliphatic hydrocarbon having 13 carbon atoms, and the description of the C14 compound can be applied to the description of the saturated aliphatic hydrocarbon having 14 carbon atoms, mutatis mutandis.

As a specific example, the above recitation "In an embodiment of the present invention, the content of the C12 compound is more than 25 mass % and 100 mass % or less. If the content of the C12 compound is 25 mass % or less, expected effects of the present invention may not be exhibited. In an embodiment of the present invention, the content of the C12 compound is preferably 30 mass % or more, 40 mass % or more, 50 mass % or more, 60 mass % or more, or mass % or more" can be read to mean that "in an embodiment of the present invention, the content of the saturated aliphatic hydrocarbon having 12 carbon atoms is more than 25 mass % and 100 mass % or less in the aliphatic hydrocarbon mixture as starting materials. If the content of the saturated aliphatic hydrocarbon having 12 carbon atoms is 25 mass % or less, expected effects of the present invention may not be exhibited. In an embodiment of the present invention, the content of the saturated aliphatic hydrocarbon having 12 carbon atoms is preferably 30 mass % or more, 40 mass % or more, 50 mass % or more, 60 mass % or more, or 65 mass % or more".

In an embodiment of the present invention, the preparation of a saturated aliphatic hydrocarbon mixture, as starting materials, containing the saturated aliphatic hydrocarbon having 12 carbon atoms, the saturated aliphatic hydrocarbon having 13 carbon atoms and the saturated aliphatic hydrocarbon having 14 carbon atoms, at a predetermined ratio can also be performed by referring to or combining heretofore known findings, for example by carrying out operations for separation by a conventional method (e.g. distillation), and the like.

According to an embodiment of the present invention, the secondary alcohol mixture, to which an alkylene oxide is to be added, is prepared by subjecting a saturated aliphatic hydrocarbon mixture as starting materials to an oxidation step, etc., and the saturated aliphatic hydrocarbon mixture as starting materials contains more than 25 mass % and 100 mass % or less of a saturated aliphatic hydrocarbon having 12 carbon atoms, 0 to 40 mass % of a saturated aliphatic hydrocarbon having 13 carbon atoms and 0 to 20 mass % of a saturated aliphatic hydrocarbon having 14 carbon atoms. By adding an alkylene oxide to the thus-prepared secondary alcohol mixture, a surfactant composition can be produced.

Addition of Alkylene Oxide

In an embodiment of the present invention, a method for producing a surfactant composition comprises adding an alkylene oxide to a secondary alcohol mixture which is prepared by, for example, the above-described method and contains: more than 25 mass % and 100 mass % or less of a C12 precursor of the following formula (2):

[Formula 4]

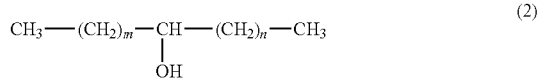

(2)

, where m+n is 9; 0 to 40 mass % of a C13 precursor of the formula (2), where m+n is 10; and 0 to 20 mass % of a C14 precursor of the formula (2), where m+n is 11. According to such a production method, it is possible to produce a surfactant composition having a high penetrating effect and a good foam breaking property.

Descriptions of the preferred contents (content ratios (mass %)) of the precursors, and the ranges, upper limits and lower limits thereof in the secondary alcohol mixture are omitted here because descriptions given in the section <Surfactant Composition>above are also applied thereto. More specifically, the description of the C12 compound can be applied to the description of the C12 precursor, the description of the C13 compound can be applied to the description of the C13 precursor, and the description of the C14 compound can be applied to the description of the C14 precursor, mutatis mutandis. More specifically, they can be applied by reading the saturated aliphatic hydrocarbon mixture as starting materials as the secondary alcohol mixture in the specific examples described in [Saturated aliphatic hydrocarbon mixture as starting materials].

In an embodiment of the present invention, the addition of an alkylene oxide can be performed by referring to or combining heretofore known findings. Heretofore known examples include methods described in, for example, JP-2003-221593 A, JP-S48-34807 and "Oil Chemistry", 24, 7, p.p. 427-434 (1975). The addition of an alkylene oxide will now be described by giving specific examples without limitation, but is not limited thereto.

In an embodiment of the present invention, ethylene oxide, propylene oxide or the like is suitable as an alkylene oxide. In an embodiment of the present invention, nitrogen purge is performed before an alkylene oxide is added. The initial nitrogen pressure in nitrogen purge is preferably 0.05 to 1.0 MPa, more preferably 0.05 to 0.4 MPa. In an embodiment of the present invention, the reaction temperature is preferably 40 to 100° C., more preferably 40 to 70° C. In an embodiment of the present invention, the number of moles of an alkylene oxide fed per 1 mole of hydroxyl groups in the secondary alcohol mixture is preferably 1 to 5, more preferably 2 to 4. The catalyst is preferably an acid catalyst such as boron trifluoride or tris(pentafluorophenyl) borane. By washing the resulting oil layer with an aqueous solution of sodium hydroxide, potassium hydroxide or the like after the reaction, the catalyst and by-produces can be removed to obtain an alkylene oxide adduct. It is preferable to remove an unreacted alcohol by performing distillation for further enhancing the purity. By adding an alkali compound such as sodium hydroxide or potassium hydroxide to the resulting alkylene oxide adduct, and performing an addition reaction with the alkylene oxide again, an alkylene oxide adduct suitable for use in a detergent composition can be obtained. The average number of moles of the alkylene oxide added is preferably 5 to 50, more preferably 6 to 30, still more preferably 7 to 15, even more preferably 9 to 12, per 1 mole of hydroxyl groups.

Applications of Surfactant Composition

In an embodiment of the present invention, with regard to applications of the surfactant composition, use as a detergent is desirable because the surfactant composition of the present invention has a high penetrability and a good foam breaking property.

In an embodiment of the present invention, the surfactant composition may be used alone, heretofore known other surfactants may be used in combination. Examples of such surfactants include anionic surfactants such as alkylbenzene sulfonic acid salts, alkyl sulfuric acid ester salts, α-olefin sulfonic acid salts, alkyl sulfonic acid salts, aliphatic amidosulfonic acid salts, dialkyl sulfosuccinic acid salts and alkyl ether sulfuric ester salts, cationic surfactants such as alkylamine salts and quaternary ammonium salts, and amphoteric surfactants such as alkylbetaines.

In an embodiment of the present invention, various additives can be added to the surfactant composition. Examples of such additives include alkaline agents, builders, perfumes, fluorescent bleaching agents, coloring agents, foaming agents, foam stabilizers, polishing agents, bactericides, bleaching agents, enzymes, antiseptic agents, dyes and solvents.

In an embodiment of the present invention, when used as a detergent, the surfactant composition can be effectively used as detergents for clothes, fiber products, eating utensils, containers, miscellaneous goods and fixings, food products, building maintenance products, dwelling houses, furniture, automobiles, aircrafts and metallic products, shampoo, body shampoo and the like.

In an embodiment of the present invention, the surfactant composition may be used as an emulsifier. Regarding oily substances for which an emulsifier can be used, there is no particular limitation, and mineral oil, animal and vegetable oils and synthetic oil can be used.

One of these substances can be used alone, or two or more thereof can be mixed and used. Examples of the mineral oil include spindle oil, machine oil and liquid paraffin oil. Examples of the animal and vegetable oils include beef fat, pork fat, fish oil, whale oil, rape seed oil, sesame oil, coconut oil, soybean oil, palm oil, camellia oil and castor oil. In an embodiment of the present invention, the emulsifier can be used for agricultural chemicals, metalworking oil, paints, emulsifiers for emulsion polymerization, and the like.

EXAMPLES

Hereinafter, the present invention will be described in more detail by way of Examples and Comparative Examples. However, the present invention should not be understood only on the basis of these Examples and Comparative Examples, and Examples obtained by appropriately combining technical means disclosed in Examples are also within the scope of the present invention.

Example 1

Oxidation Step and Alcoholization Step 1000 g of a mixture of saturated aliphatic hydrocarbons having a carbon number distribution as shown in Table 1 below, and 25 g of metaboric acid were put in a 3 L-volume cylindrical reactor, and subjected to an oxidation reaction at 170° C. at ordinary pressure for 2 hours by injecting a gas having an oxygen concentration of 3.5 vol % and a nitrogen concentration of 96.5 vol % at a rate of 430 L per hour.

50 mass % of the oxidation reaction mixed liquid was hydrolyzed with a large amount of hot water (95° C.), and an oil layer containing the formed alcohol was separated. The remaining 50% of the oxidation reaction liquid was mixed with this oil layer to make an adjustment so that 1.04 equivalents of the boric acid ester compound in terms of an orthoboric acid ester was present. The resulting mixture was treated at 200 hPa and 170° C. to esterify the alcohol contained therein with orthoboric acid. The mixture containing an orthoboric acid ester was subjected to flash distillation at 7 hPa to remove unreacted saturated aliphatic hydrocarbons until the temperature of the residual liquid was 170° C. Subsequently, the residual liquid was hydrolyzed with a large amount of hot water at 95° C. to remove the boric acid to the aqueous phase. The resulting oil layer was saponified, and washed with water to remove organic acids and organic acid esters. This oil phase was subjected to fractional distillation at 7 hPa. The fraction having a boiling point in the range of 95° C. or higher and lower than 120° C. as the first fraction was a mixture of a small amount of paraffin, a carbonyl compound and a monohydric primary alcohol. The second fraction (a fraction having a boiling point in the range of 120 to 150° C.) consisted mostly of a monohydric secondary alcohol while including a very small amount of a carbonyl compound and a polyhydric secondary alcohol. As this second fraction, a monohydric secondary alcohol was obtained. In the manner described above, a secondary alcohol mixture was obtained.

Alkylene Oxide Adding Step

In a SUS 3 L autoclave with a stirrer, thermometer and an inlet tube for introducing ethylene oxide (EO), 1 kg of the secondary alcohol mixture obtained as described above was placed, and nitrogen purge was performed. Thereafter, 1.68 g of a $BF_3$-Et catalyst (BF3: 46 to 49%) was placed in the autoclave, and ethylene oxide (EO) was fed in an amount of 1.7 moles per 1 mole of hydroxyl groups at 55±5° C. at an initial nitrogen pressure of 0.05 MPa to add the ethylene oxide. Thereafter, the reaction liquid was washed at 90° C. by adding a NaOH solution, and washed with water to a pH of 7 or less. Subsequently, the oil phase was placed in a 3 L three-necked glass flask, a distillation tower (filling material: Packing Dixon with an inner diameter of 40 mm, a length of 200 mm and a theoretical stage number of 3) was attached, and distillation was performed to obtain an ethoxylate adduct in an amount of 3 moles per 1 mole of hydroxyl groups in terms of an average number of moles added. In the same type of autoclave as described above, 558 g of the resulting ethoxylate adduct and 1 g of potassium hydroxide were placed, and nitrogen purge was performed. The pressure inside the reactor was then set to 15 kPa with nitrogen, and the mixture was heated at 150° C. to react 442 g of ethylene oxide. After the reaction, the reaction product was neutralized with acetic acid to obtain a surfactant which is an ethylene oxide adduct. It was confirmed that the resulting surfactant composition was represented by the formula (1), and that the contents of a C12 compound with m+n being 9, a C13 compound with m+n being 10 and a C14 compound with m+n being 11 (hereinafter, referred to as a carbon number distribution) were as shown in Table 1. The average number of moles of EO added was found to be 8.6 by the following method for measuring a hydroxyl value.

Comparative Examples 1 and 2

Surfactant compositions which were ethoxylate adducts were obtained in the same manner as in Example 1 except that the mixture of saturated aliphatic hydrocarbons in Example 1 was changed as shown in Table 1 below. It was confirmed that the resulting surfactant compositions were each represented by the formula (1), and that the carbon number distributions of the surfactant compositions of Comparative Examples 1 and 2 were as shown in Table 1. The average numbers of moles of EO added were found to be 9.0 and 9.4, respectively, by the following method for measuring a hydroxyl value.

The carbon number distribution in the starting material paraffin (mixture of saturated aliphatic hydrocarbons), the carbon number distribution in the secondary alcohol (mixture of secondary alcohols) and the carbon number distribution in the alkoxylate (ethoxylate adduct) are the same.

Evaluation Method

Method for Measuring Hydroxyl Value 444 g of phthalic anhydride of a special grade reagent was taken, and dissolved in pyridine of a special grade reagent to prepare a total volume of 3 L of a phthalation reagent. About 1 g of a sample was precisely weighed and taken in a Teflon flask, 9 mL of the phthalation reagent was added, and the flask was capped with a Teflon lid. Here, a flask having no sample was used as a blank test. The flask was placed on a hot plate whose surface temperature was adjusted to 120° C., and the sample was heated for 90 minutes. During heating, the flask was lightly shaken every 15 minutes to stir the sample. After the heating, 15 mL of pure water was added, the resulting mixture was allowed to cool for 10 minutes, 50 mL of pure water was then added, and the resulting mixture was lightly stirred. The flask was set in an automatic titrator (AT-610 manufactured by KYOTO ELECTRONICS INDUSTRY CO., LTD.), and neutralization titration was performed with a 0.5 mol/L potassium hydroxide solution (volumetric solution for volumetric analysis manufactured by KANTO KAGAKU). Measurement was performed in triplicate per sample, and the hydroxyl value was calculated from the following equation.

$HV=\{(VB-VS) \times N \times F \times 56.11\}/S$

HV: hydroxyl value (mg KOH/g)
VB: titer with 0.5 mol/L of aqueous potassium hydroxide solution in blank test (mL)
VS: titer with 0.5 mol/L aqueous potassium hydroxide solution for sample (mL)
N: 0.5 (concentration of aqueous potassium hydroxide solution (mol/L))
F: factor of aqueous potassium hydroxide solution at 0.5 mol/L
S: amount of sample collected (g)

From the resulting hydroxyl value, the average molecular weight was calculated, and from a difference between this average molecular weight and the average molecular weight of the secondary alcohol, the average number of moles of EO added was calculated.

$n=(56110/HV-Mw)/44.05$

Mw: average molecular weight of secondary alcohol

Method for Measuring Carbon Number Distribution in Saturated Aliphatic Hydrocarbon The carbon number distribution in the saturated aliphatic hydrocarbon was measured under the following conditions by using the following apparatus.
Apparatus: GC-2010 (SHIMADZU)
Conditions: column: UA1 (MS/HT)-30M-0.25F (GL Science)
Injection amount: 0.5 ml
Injection method: splitless
Injection temperature: 400° C.
Column temperature: 50° C. (10 min) to 5° C./min-400° C. (30 min)
Carrier gas: He, 1 ml/min
Detector: FID (400° C., H2 50 ml/min, Air 400 ml/min, N2 20 ml/min)

Method for Measuring Carbon Number Distribution in Surfactant Composition

Apparatus: Alliance 2695 HPLC (Waters)
Column: Intersil ODS-2 having an inner diameter of 3.0 mm and a length of 150 mm (GL Science)
Column temperature: 40° C.
Injection amount: 100 μl
Sample concentration: 2%
Eluent: acetonitrile/water =65/35 (vol %)
Flow rate: 1 ml/min
Detector: RI

HLB

HLBs of the surfactant compositions of Examples and Comparative Examples are shown in Table 1. The HLBs are values determined by the Griffin method. According to an embodiment of the present invention, the HLB of the surfactant composition is preferably 10.0 to 16.0, more preferably 11.0 to 15.0, still more preferably 12.0 to 14.0.

(1) Penetrability

The penetrability was evaluated by a canvas disc method. 500 ml of a surfactant composition aqueous solution was placed in a beaker (outer diameter: 87 mm), a test cloth was put on the aqueous solution, and the test cloth was then promptly submerged in the solution by using a Gooch glass funnel (barrel outer diameter: 45 mm, leg outer diameter: 33 mm, barrel length: 80 mm). The time taken for the test cloth to be impregnated with the aqueous solution to remove bubbles to thereby settle to the bottom of the beaker was measured.

The measurement was performed in triplicate. Table 1 shows the arithmetic average values thereof.

Conditions

Concentration of surfactant composition in water: 0.1 wt %
Test cloth: cotton, No. 6 canvas (diameter: 25 mm)

(2) Foam Breaking Property

The foam breaking property was evaluated by using Tergot-O-Meter Model TM-4 (DAIEI KAGAKU SEIKI MFG. co., ltd.) as an apparatus. Specifically, washing was performed under the following washing conditions, rinsing was performed under the following conditions, and evaluation was performed in the following manner.

Washing Conditions

Cloth: 30 g of cotton (5×5 $cm^2$)
Concentration of surfactant composition in water: 0.05 wt %
Water: 900 g (specifically, adjusted to Ca: 1.5 mmol/L and Mg: 1.0 mmol/L)
Temperature of water containing surfactant composition: 30° C.
Stirring rate: 120 rpm
Washing time: 20 min Rinsing Conditions Temperature: 30° C.
Water: 900 g of pure water
Stirring rate: 120 rpm
Rinsing time: 5 min Evaluation Washing and rinsing were each performed once, a single cotton cloth and 50 g of pure water were then put in a 100 ml sample tube, and shaken, and the state of foam was observed.

TABLE 1

| | Carbon number distribution in mixture of saturated aliphatic hydrocarbons (mass %) | EO | HLB | Evaluation (1) Penetrability | | Evaluation (2) Foam breaking property | |
|---|---|---|---|---|---|---|---|
| | | | | Penetration time (sec) | Evaluation | Foam after rinsing | Evaluation |
| Example 1 | C12/C13/C14 = 70/20/10 | 8.6 mol | 13.3 | 33.0 | ○ | Little | ○ |
| Comparative Example 1 | C12/C13/C14 = 20/55/25 | 9.0 mol | 13.3 | 41.0 | Δ | Present | X |
| Comparative Example 2 | C12/C13/C14 = 10/20/70 | 9.4 mol | 13.3 | 49.0 | X | Present | X |

Thus, as the second invention, the following embodiments are provided.

[1.]

A surfactant composition comprising: a C12 compound of the following formula (1):

[Formula 1]

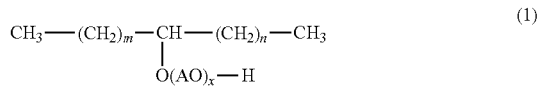

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is more than 25 mass % and 100 mass % or less, the content of the C13 compound is 0 to 40 mass %, and the content of the C14 compound is 0 to 20 mass %.

[2.]

The surfactant composition according to [1.], wherein the alkylene group is an ethylene group.

[3.]

The surfactant composition according to [1.] or [2.], wherein the content of the C12 compound is 50 mass % or more.

[4.]

A method for producing a surfactant composition, comprising adding an alkylene oxide to a secondary alcohol mixture containing: more than 25 mass % and 100 mass % or less of a C12 precursor of the following formula (2):

[Formula 2]

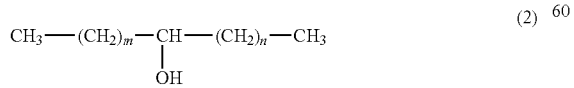

where m+n is 9; 0 to 40 mass % of a C13 precursor of the formula (2), where m+n is 10; and 0 to 20 mass % of a C14 precursor of the formula (2), where m+n is 11.

THIRD INVENTION

Subsequently, the third invention will be described.

[Title of Invention] SURFACTANT COMPOSITION AND METHOD FOR PRODUCING SAME

TECHNICAL FIELD

The present invention relates to a surfactant composition, and a method for producing the surfactant composition.

BACKGROUND ART

Higher secondary alcohol ethoxylates are widely used as nonionic surfactants because they have a low pour point, and are easy to handle. As a known example, there is, for example, a detergent composition which is aimed at improving detergency and comprises a nonionic surfactant containing a higher secondary alcohol alkoxylate adduct represented by a specific chemical formula, and a primary alcohol alkoxylate, an anionic surfactant or a cationic surfactant (for example, Patent Literature 1).

CITATION LIST

Patent Literature

[Patent Literature 1] JP-H11-349984 A

SUMMARY OF INVENTION

Technical Problem

On the other hand, the present inventors have found that in the contemporary society, there is a need for surfactant compositions which not only deliver basic performance such as detergency, but also meet a new challenge of reducing the odor.

Accordingly, an object of the present invention is to provide a novel surfactant composition which enables improvement of detergency and has a reduced odor.

Means for Solving Problem

The above-described problem can be solved by the following invention.

A surfactant composition comprising: a C12 compound of the following formula (1):

[Formula 1]

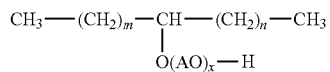

$$CH_3\text{—}(CH_2)_m\text{—}CH\text{—}(CH_2)_n\text{—}CH_3 \quad (1)$$
$$\underset{O(AO)_x\text{—}H}{|}$$

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is 0 to 25 mass %, the content of the C13 compound is 0 to 40 mass %, and the content of the C14 compound is more than 49.9 mass % and 100 mass % or less.

Advantageous Effect of the Invention

According to the present invention, it is possible to provide a novel surfactant composition which enables improvement of detergency and has a reduced odor.

DESCRIPTION OF EMBODIMENTS

Hereinafter, the present invention will be described. It is to be noted that the present invention is not limited to the following embodiments. Unless otherwise specified, operations and measurements of physical properties and the like are performed under the condition of room temperature (20 to 25° C.). The term "content" can be interpreted as a "content ratio" depending on context.

Surfactant Composition

A surfactant composition according to an aspect of the present invention is a surfactant composition comprising: a C12 compound of the following formula (1):

[Formula 1]

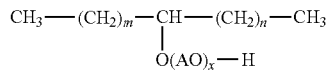

$$CH_3\text{—}(CH_2)_m\text{—}CH\text{—}(CH_2)_n\text{—}CH_3 \quad (1)$$
$$\underset{O(AO)_x\text{—}H}{|}$$

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is 0 to 25 mass %, the content of the C13 compound is 0 to 40 mass %, and the content of the C14 compound is more than 49.9 mass % and 100 mass % or less. Such a surfactant composition (sometimes referred to as a "detergent composition") is a surfactant composition which improves detergency and has a reduced odor.

In an embodiment of the present invention, the alkylene group having 1 to 3 carbon atoms is preferably an ethylene group or a propylene group, more preferably an ethylene group. By such an embodiment, a surfactant composition having high detergency can be obtained at low cost.

In an embodiment of the present invention, x is preferably 5 to 50, more preferably 6 to 30, still more preferably 7 to 15, even more preferably 9 to 12. By such an embodiment, solubility in water and affinity to oil can be imparted to exhibit excellent detergency. The C12 compound, the C13 compound and the C14 compound may differ in A and x.

In an embodiment of the present invention, the content of the C12 compound is 0 to 25 mass %. If the content of the C12 compound is more than 25 mass %, expected effects of the present invention may not be exhibited. In an embodiment of the present invention, the content of the C12 compound is preferably 2 mass % or more, 4 mass % or more, 6 mass % or more, or 8 mass % or more. By such an embodiment, the technical effect of improving the fluidity of a liquid detergent is obtained. In an embodiment of the present invention, the content of the C12 compound is less than 25 mass %, 20 mass % or less, less than 20 mass %, 19 mass % or less, 18 mass % or less, 17 mass % or less, 16 mass % or less, 15 mass % or less, or 12 mass % or less. By such an embodiment, the technical effect of improving detergency is obtained.

In an embodiment of the present invention, the content of the C13 compound is 0 to 40 mass %. If the content of the C13 compound is more than 40 mass %, expected effects of the present invention may not be exhibited. In an embodiment of the present invention, the content of the C13 compound is more preferably more than 0 mass %, 5 mass % or more, 10 mass % or more, 15 mass % or more, or 18 mass % or more. By such an embodiment, the technical effect of improving the fluidity of a liquid detergent is obtained. In an embodiment of the present invention, the content of the C13 compound is preferably 35 mass % or less, 30 mass % or less, 25 mass % or less, or 23 mass % or less. By such an embodiment, the technical effect of improving detergency is obtained.

In an embodiment of the present invention, the content of the C14 compound is more than 49.9 mass % and 100 mass % or less. If the content of the C14 compound is 49.9 mass % or less, expected effects of the present invention may not be exhibited. In an embodiment of the present invention, the content of the C14 compound is preferably 50 mass % or more, 55 mass % or more, 60 mass % or more, or 65 mass % or more. By such an embodiment, the technical effect of improving detergency is obtained. In an embodiment of the present invention, the content of the C14 compound is preferably less than 100 mass %, 90 mass % or less, 85 mass % or less, 80 mass % or less, or 75 mass % or less. By such an embodiment, the technical effect of improving the fluidity of a liquid detergent is obtained.

In an embodiment of the present invention, the total of the content of the C12 compound, the content of the C13 compound and the content of the C14 compound is 100 mass %.

While various upper limits, lower limits and ranges of contents (content ratios) are disclosed herein, it should be appreciated that all the upper limits, lower limits, ranges or combinations thereof are disclosed herein. That is, they warrant the legality of amendments.

Method for Producing Surfactant Composition

In an embodiment of the present invention, a method for producing a surfactant composition comprises adding an alkylene oxide to a secondary alcohol mixture containing: 0 to 25 mass % of a C12 precursor of the following formula (2):

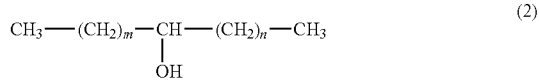

[Formula 3]

$$CH_3-(CH_2)_m-\underset{OH}{CH}-(CH_2)_n-CH_3 \quad (2)$$

where m+n is 9; 0 to 40 mass % of a C13 precursor of the formula (2), where m+n is 10; and more than 49.9 mass % and 100 mass % or less of a C14 precursor of the formula (2), where m+n is 11. According to such a production method, it is possible to produce a surfactant composition which enables improvement of detergency and has a reduced odor.

Preparation of Secondary Alcohol Mixture

In an embodiment of the present invention, the secondary alcohol mixture of the formula (2) can be obtained by carrying out an oxidation step of oxidizing a saturated aliphatic hydrocarbon mixture as starting materials, and an alcoholization step.

In an embodiment of the present invention, the oxidation step can be carried out by referring to or combining heretofore known findings. It is possible to appropriately refer to or combine descriptions concerning the oxidation step in, for example, JP-S48-34807 A and "Oil Chemistry", 24, 7, p.p. 427-434 (1975), but the method for carrying out the oxidation step is not limited thereto. An exemplary method will be now described. A saturated aliphatic hydrocarbon mixture as starting materials is subjected to an oxidation reaction by injecting a gas containing oxygen and nitrogen in the presence of a boron compound. As the boron compound, metaboric acid, orthoboric acid or the like is suitable. Subsequently, an alcohol prepared through hydrolysis by hot-water treatment or the like is esterified with orthoboric acid. Preferably, the alcohol is reacted with boric acid under the conditions of 10 to 300 hPa and 150 to 190° C. to perform the esterification with orthoboric acid. By subjecting the mixture containing an orthoboric acid ester to flash distillation preferably at 1 to 100 hPa, unreacted saturated aliphatic hydrocarbons can be removed. Subsequently, a hydrolysis step of hydrolyzing residues on distillation to separate the residues into boric acid and an organic acid layer is carried out, followed by performing saponification in which the separated organic layer is saponified with an alkali to be separated into an alkali aqueous solution layer and a crude alcohol layer. In addition, water washing is performed to remove organic acids and organic acid esters. Thereafter, fractional distillation is performed to obtain a secondary alcohol mixture.

Thus, in an embodiment of the present invention, the oxidation step includes subjecting a saturated aliphatic hydrocarbon mixture as starting materials for the present invention to an oxidation reaction by adding a gas containing oxygen and nitrogen in the presence of a boron compound. An embodiment of the present invention includes preparing a mixture containing an orthoboric acid ester by esterifying an alcohol, which is formed by the oxidation reaction, with orthoboric acid. An embodiment of the present invention includes distilling the mixture containing an orthoboric acid ester to remove unreacted saturated aliphatic hydrocarbons. In an embodiment of the present invention, a hydrolysis step of hydrolyzing resides on distillation to separate the residues into boric acid and an organic layer is carried out. An embodiment of the present invention includes subjecting the separated organic layer to saponification with an alkali, more specifically saponification for separation into an alkali aqueous solution layer and a crude alcohol layer, and also performing water washing. An embodiment of the present invention includes removing organic acids and organic acid esters, and then performing fractional distillation to obtain a secondary alcohol mixture.

Saturated Aliphatic Hydrocarbon Mixture as Starting Materials

Here, the saturated aliphatic hydrocarbon mixture as starting materials serves as starting materials for obtaining a secondary alcohol mixture of the formula (2). In an embodiment of the present invention, the saturated aliphatic hydrocarbon mixture as starting materials contains a saturated aliphatic hydrocarbon having 12 carbon atoms, a saturated aliphatic hydrocarbon having 13 carbon atoms and a saturated aliphatic hydrocarbon having 14 carbon atoms, at a predetermined ratio.

Specifically, the saturated aliphatic hydrocarbon mixture as starting materials contains 0 to 25 mass % of a saturated aliphatic hydrocarbon having 12 carbon atoms (which corresponds to the C12 compound), 0 to 40 mass % of a saturated aliphatic hydrocarbon having 13 carbon atoms (which corresponds to the C13 compound), and more than 49.9 mass % and 100 mass % or less of a saturated aliphatic hydrocarbon having 14 carbon atoms (which corresponds to the C14 compound). Descriptions of the preferred contents (content ratios (mass %)) of the saturated aliphatic hydrocarbons having the respective numbers of carbons, and the ranges, upper limits and lower limits thereof in the saturated aliphatic hydrocarbon mixture as starting materials are omitted here because descriptions given in the section <Surfactant Composition>above are also applied thereto.

More specifically, the description of the C12 compound can be applied to the description of the saturated aliphatic hydrocarbon having 12 carbon atoms, the description of the C13 compound can be applied to the description of the saturated aliphatic hydrocarbon having 13 carbon atoms, and the description of the C14 compound can be applied to the description of the saturated aliphatic hydrocarbon having 14 carbon atoms.

As a specific example, the above recitation "In an embodiment of the present invention, the content of the C14 compound is more than 49.9 mass % and 100 mass % or less. If the content of the C14 compound is 49.9 mass % or less, expected effects of the present invention may not be exhibited. In an embodiment of the present invention, the content of the C14 compound is preferably 50 mass % or more, 55 mass % or more, 60 mass % or more, or 65 mass % or more. By such an embodiment, the technical effect of improving detergency is obtained. In an embodiment of the present invention, the content of the C14 compound is preferably less than 100 mass %, 90 mass % or less, 85 mass % or less, mass % or less, or 75 mass % or less. By such an embodiment, the technical effect of improving the fluidity of a liquid detergent is obtained" can be read to mean that "in an embodiment of the present invention, the content of the saturated aliphatic hydrocarbon having 14 carbon atoms is more than 49.9 mass % and 100 mass % or less in the saturated aliphatic hydrocarbon mixture as starting materials. If the content of the saturated aliphatic hydrocarbon having 14 carbon atoms is 49.9 mass % or less, expected effects of the present invention may not be exhibited. In an embodiment of the present invention, the content of the saturated aliphatic hydrocarbon having 14 carbon atoms is preferably 50 mass % or more, 55 mass % or more, 60 mass % or more, or 65 mass % or more. By such an embodiment, the technical effect of improving detergency is obtained. In an embodiment of the present invention, the content of the saturated aliphatic hydrocarbon having carbon atoms is preferably less than 100 mass %, 90 mass % or less, 85 mass % or less, 80 mass % or less, or 75 mass % or less. By such an embodiment, the technical effect of improving the fluidity of a liquid detergent is obtained".

In an embodiment of the present invention, the preparation of a saturated aliphatic hydrocarbon mixture as starting materials containing the saturated aliphatic hydrocarbon having 12 carbon atoms, the saturated aliphatic hydrocarbon having 13 carbon atoms and the saturated aliphatic hydrocarbon having 14 carbon atoms, at a predetermined ratio can also be performed by referring to or combining heretofore known findings, for example by carrying out operations for separation by a conventional method (e.g. distillation), and the like.

According to an embodiment of the present invention, the secondary alcohol mixture, to which an alkylene oxide is to be added, is prepared by subjecting a saturated aliphatic hydrocarbon mixture as starting materials to an oxidation step, etc., and the saturated aliphatic hydrocarbon mixture as starting materials contains 0 to 25 mass % of a saturated aliphatic hydrocarbon having 12 carbon atoms, 0 to 40 mass % of a saturated aliphatic hydrocarbon having 13 carbon atoms and more than 49.9 mass % and 100 mass % or less of a saturated aliphatic hydrocarbon having 14 carbon atoms. By adding an alkylene oxide to the thus-prepared secondary alcohol mixture, a surfactant composition can be produced.

Addition of Alkylene Oxide

In an embodiment of the present invention, a method for producing a surfactant composition comprises adding an alkylene oxide to a secondary alcohol mixture which is prepared by, for example, the above-described method and contains: 0 to 25 mass % of a C12 precursor of the following formula (2):

[Formula 4]

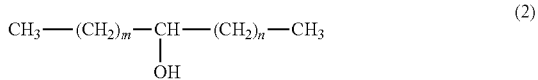

(2)

where m+n is 9; 0 to 40 mass % of a C13 precursor of the formula (2), where m+n is 10; and more than 49.9 mass % and 100 mass % or less of a C14 precursor of the formula (2), where m+n is 11. According to such a production method, it is possible to produce a surfactant composition which improves detergency and has a reduced odor.

Descriptions of the preferred contents (content ratios (mass %)) of the precursors, and the ranges, upper limits and lower limits thereof in the secondary alcohol mixture are omitted here because descriptions given in the section <Surfactant Composition>above are also applied thereto. More specifically, the description of the C12 compound of can be applied to the description of the C12 precursor, the description of the C13 compound can be applied to the description of the C13 precursor, and the description of the C14 compound can be applied to the description of the C14 precursor, mutatis mutandis. More specifically, they can be applied by reading the saturated aliphatic hydrocarbon mixture as starting materials as the secondary alcohol mixture in the specific examples described in [Saturated aliphatic hydrocarbon mixture as starting materials].

In an embodiment of the present invention, the addition of an alkylene oxide can be performed by referring to or combining heretofore known findings. Heretofore known examples include methods described in, for example, JP-2003-221593 A, JP-S48-34807 and "Oil Chemistry", 24, 7, p.p. 427-434 (1975). The addition of an alkylene oxide will now be described by giving specific examples, but is not limited thereto.

In an embodiment of the present invention, ethylene oxide, propylene oxide or the like is suitable as an alkylene oxide. In an embodiment of the present invention, nitrogen purge is performed before an alkylene oxide is added. The initial nitrogen pressure in nitrogen purge is preferably 0.05 to 1.0 MPa, more preferably 0.05 to 0.4 MPa. In an embodiment of the present invention, the reaction temperature is preferably 40 to 100° C., more preferably 40 to 70° C. In an embodiment of the present invention, the number of moles of an alkylene oxide fed per 1 mole of hydroxyl groups in the secondary alcohol mixture is preferably 1 to 5, more preferably 2 to 4. The catalyst is preferably an acid catalyst such as boron trifluoride or tris(pentafluorophenyl) borane. By washing the resulting oil layer with an aqueous solution of sodium hydroxide, potassium hydroxide or the like after the reaction, the catalyst and by-produces can be removed to obtain an alkylene oxide adduct. It is preferable to remove an unreacted alcohol by performing distillation for further enhancing the purity. By adding an alkali compound such as sodium hydroxide or potassium hydroxide to the resulting alkylene oxide adduct, and performing an addition reaction with the alkylene oxide again, an alkylene oxide adduct suitable for use in a detergent composition can be obtained. The average number of moles of the alkylene oxide added is preferably 5 to 50, more preferably 6 to 30, still more preferably 7 to 15, even more preferably 9 to 12, per 1 mole of hydroxyl groups.

Applications of Surfactant Composition

In an embodiment of the present invention, with regard to applications of the surfactant composition, use as a detergent is desirable because the surfactant composition of the present invention is excellent in detergency and has a reduced odor.

In an embodiment of the present invention, the surfactant composition may be used alone, or heretofore known other surfactants may be used in combination. Examples of such surfactants include anionic surfactants such as alkylbenzene sulfonic acid salts, alkyl sulfuric acid ester salts, α-olefin sulfonic acid salts, alkyl sulfonic acid salts, aliphatic amidosulfonic acid salts, dialkyl sulfosuccinic acid salts and alkyl ether sulfuric ester salts, cationic surfactants such as alkylamine salts and quaternary ammonium salts, and amphoteric surfactants such as alkylbetaines.

In an embodiment of the present invention, various additives can be added to the surfactant composition. Examples of such additives include alkaline agents, builders, perfumes, fluorescent bleaching agents, coloring agents, foaming agents, foam stabilizers, polishing agents, bactericides, bleaching agents, enzymes, antiseptic agents, dyes and solvents.

In an embodiment of the present invention, when used as a detergent, the surfactant composition can be effectively used as detergents for clothes, fiber products, eating utensils, containers, miscellaneous goods and fixings, food products, building maintenance products, dwelling houses, furniture, automobiles, aircrafts and metallic products, shampoo, body shampoo and the like.

In an embodiment of the present invention, the surfactant composition may be used as an emulsifier. Regarding oily substances for which the emulsifier can be used, there is no particular limitation, and mineral oil, animal and vegetable oils and synthetic oil can be used. One of these substances can be used alone, or two or more thereof can be mixed and used. Examples of the mineral oil include spindle oil, machine oil and liquid paraffin oil. Examples of the animal and vegetable oils include beef fat, pork fat, fish oil, whale oil, rape seed oil, sesame oil, coconut oil, soybean oil, palm oil, camellia oil and castor oil. In an embodiment of the present invention, the emulsifier can be used for agricultural chemicals, metalworking oil, paints, emulsifiers for emulsion polymerization, and the like.

EXAMPLES

Hereinafter, the present invention will be described in more detail by way of Examples and Comparative Examples.

However, the present invention should not be understood only on the basis of these Examples and Comparative Examples, and Examples obtained by appropriately combining technical means disclosed in Examples are also within the scope of the present invention.

Example 1

Oxidation Step and Alcoholization Step 1000 g of a mixture of saturated aliphatic hydrocarbons having a carbon number distribution as shown in Table 1 below, and 25 g of metaboric acid were put in a 3 L-volume cylindrical reactor, and subjected to an oxidation reaction at 170° C. at ordinary pressure for 2 hours by injecting a gas having an oxygen concentration of 3.5 vol % and a nitrogen concentration of 96.5 vol % at a rate of 430 L per hour.

50 mass % of the oxidation reaction mixed liquid was hydrolyzed with a large amount of hot water (95° C.), and an oil layer containing the formed alcohol was separated. The remaining 50% of the oxidation reaction liquid was mixed with this oil layer to make an adjustment so that 1.04 equivalents of a boric acid ester compound in terms of an orthoboric acid ester was present. The resulting mixture was treated at 200 hPa and 170° C. to esterify the alcohol contained therein with orthoboric acid. The mixture containing an orthoboric acid ester was subjected to flash distillation at 7 hPa to remove unreacted saturated aliphatic hydrocarbons until the temperature of the residual liquid was 170° C. Subsequently, the residual liquid was hydrolyzed with a large amount of hot water at 95° C. to remove the boric acid to the aqueous phase. The resulting oil layer was saponified, and washed with water to remove organic acids and organic acid esters. This oil phase was subjected to fractional distillation at 7 hPa. The fraction having a boiling point in the range of 95° C. or higher and lower than 120° C. as the first fraction was a mixture of a small amount of paraffin, a carbonyl compound and a monohydric primary alcohol. The second fraction (a fraction having a boiling point in the range of 120 to 150° C.) consisted mostly of a monohydric secondary alcohol while including a very small amount of a carbonyl compound and a polyhydric secondary alcohol. As this second fraction, a monohydric secondary alcohol was obtained. In the manner described above, a secondary alcohol mixture was obtained.

Alkylene Oxide Adding Step

In a SUS 3 L autoclave with a stirrer, thermometer and an inlet tube for introducing ethylene oxide (EO), 1 kg of the secondary alcohol mixture obtained as described above was placed, and nitrogen purge was performed. Thereafter, 1.68 g of a $BF_3$-Et catalyst ($BF_3$: 46 to 49%) was placed in the autoclave, and ethylene oxide (EO) was fed in an amount of 1.7 moles per 1 mole of hydroxyl groups at 55±5° C. at an initial nitrogen pressure of 0.05 MPa to add the ethylene oxide. Thereafter, the reaction liquid was washed at 90° C. by adding a NaOH solution, and washed with water to a pH of 7 or less. Subsequently, the oil phase was placed in a 3 L three-necked glass flask, a distillation tower (filling material: Packing Dixon with an inner diameter of 40 mm, a length of 200 mm and a theoretical stage number of 3) was attached, and distillation was performed to obtain an ethoxylate adduct in an amount of 3 moles per 1 mole of hydroxyl groups in terms of an average number of moles added. In the same type of autoclave as described above, 558 g of the resulting ethoxylate adduct and 1 g of potassium hydroxide were placed, and nitrogen purge was performed. The pressure inside the reactor was then set to 15 kPa with nitrogen, and the mixture was heated at 150° C. to react 442 g of ethylene oxide. After the reaction, the reaction product was neutralized with acetic acid to obtain a surfactant which is an ethylene oxide adduct. It was confirmed that the resulting surfactant composition was represented by the formula (1), and that the contents of a C12 compound with m+n being 9, a C13 compound with m+n being 10 and a C14 compound with m+n being 11 (hereinafter, referred to as a carbon number distribution) were as shown in Table 1. The average number of moles of EO added was found to be 9.4 by the following method for measuring a hydroxyl value.

Comparative Examples 1 and 2

Surfactant compositions which were ethoxylate adducts were obtained in the same manner as in Example 1 except that the mixture of saturated aliphatic hydrocarbons in Example 1 was changed as shown in Table 1 below. It was confirmed that the resulting surfactant compositions were each represented by the formula (1), and that the carbon number distributions of the surfactant compositions of Comparative Examples 1 and 2 were as shown in Table 1. The average numbers of moles of EO added were found to be 9.0 and 8.6, respectively, by the following method for measuring a hydroxyl value.

The carbon number distribution in the starting material paraffin (mixture of saturated aliphatic hydrocarbons), the carbon number distribution in the secondary alcohol (mixture of secondary alcohols) and the carbon number distribution in the alkoxylate (ethoxylate adduct) are the same.

Evaluation Method

Method for Measuring Hydroxyl Value 444 g of phthalic anhydride of a special grade reagent was taken, and dissolved in pyridine of a special grade reagent to prepare a total volume of 3 L of a phthalation reagent. About 1 g of a sample was precisely weighed and taken in a Teflon flask, 9 mL of the phthalation reagent was added, and the flask was capped with a Teflon lid. Here, a flask having no sample was used as a blank test. The flask was placed on a hot plate whose surface temperature was adjusted to 120° C., and the sample was heated for 90 minutes. During heating, the flask was lightly shaken every 15 minutes to stir the sample. After the heating, 15 mL of pure water was added, the resulting mixture was allowed to cool for 10 minutes, 50 mL of pure water was then added, and the resulting mixture was lightly stirred. The flask was set in an automatic titrator (AT-610 manufactured by KYOTO ELECTRONICS INDUSTRY CO., LTD.), and neutralization titration was performed with a 0.5 mol/L potassium hydroxide solution (volumetric solution for volumetric analysis manufactured by KANTO KAGAKU). Measurement was performed in triplicate per sample, and the hydroxyl value was calculated from the following equation.

$$HV=\{(VB-VS)\times N\times F\times 56.11\}/S$$

HV: hydroxyl value (mg KOH/g)
VB: titer with 0.5 mol/L aqueous potassium hydroxide solution in blank test (mL)
VS: titer with 0.5 mol/L aqueous potassium hydroxide solution for in sample (mL)
N: 0.5 (concentration of aqueous potassium hydroxide solution (mol/L))
F: factor of aqueous potassium hydroxide solution at 0.5 mol/L
S: amount of sample collected (g)

From the resulting hydroxyl value, the average molecular weight was calculated, and from a difference between this average molecular weight and the average molecular weight of the secondary alcohol, the average number of moles of EO added was calculated.

$$n=(56110/HV-Mw)/44.05$$

Mw: average molecular weight of secondary alcohol

Method for Measuring Carbon Number Distribution in Saturated Aliphatic Hydrocarbon The carbon number distribution in the saturated aliphatic hydrocarbon was measured under the following conditions by using the following apparatus.
Apparatus: GC-2010 (SHIMADZU)
Conditions: column: UA1 (MS/HT)-30M-0.25F (GL Science)
Injection amount: 0.5 ml
Injection method: splitless
Injection temperature: 400° C.
Column temperature: 50° C. (10 min) to 5° C./min-400° C. (30 min)
Carrier gas: He, 1 ml/min
Detector: FID (400° C., $H_2$ 50 ml/min, Air 400 ml/min, $N_2$ 20 ml/min)

Method for Measuring Carbon Number Distribution in Surfactant Composition

Apparatus: Alliance 2695 HPLC (Waters)
Column: Intersil ODS-2 having an inner diameter of 3.0 mm and a length of 150 mm (GL Science)
Column temperature: 40° C.
Injection amount: 100 μl
Sample concentration: 2%
Eluent: acetonitrile/water =65/35 (vol %)
Flow rate: 1 ml/min
Detector: RI

HLB

HLBs of the surfactant compositions of Examples and Comparative Examples are shown in Table 1. The HLBs are values determined by the Griffin method. According to an embodiment of the present invention, the HLB of the surfactant composition is preferably 10.0 to 16.0, more preferably 11.0 to 15.0, still more preferably 12.0 to 14.0.

(1) Detergency

A test on detergency was conducted under the following conditions by referring to JIS K-3362: 2008. Specifically, first, a contaminant was provided. The contaminant has the composition of oleic acid: 28.3 mass %, triolein: 15.6 mass %, cholesterol oleate: 12.2 mass %, liquid paraffin: 2.5 mass %, squalene: 2.5 mass %, cholesterol: 1.6 mass %, gelatin: 7.0 mass %, red-yellow soil: 29.8 mass % and carbon black: 0.5 mass %.

This contaminant was applied to a cloth (5 cm×5 cm) to prepare a contaminated cloth. Five contaminated cloths were prepared in the same manner. Thus, a total of six contaminated cloths were prepared.

The total of six contaminated cloths and 30 g of cotton were immersed in 900 g of water (30° C.) containing Ca at 1.5 mmol/L and Mg at 1.0 mmol/L. A surfactant composition was added to the water (30° C.) to a concentration of 0.05 wt %. Thereafter, washing was performed at a stirring rate of 120 rpm for 20 minutes.

Before and after the washing, the reflectance of the contaminated cloth was measured at four points (two points on each of the front and the back) for each test cloth, and from the average value thereof (a total of 24 points), the difference in reflectance between before and after the washing (ΔZ) was evaluated. The reflectance was measured by using a color-difference meter (Spectral Color-Difference Meter SA 5500 (manufactured by DENSHOKU INDUSTRIES Co., Ltd.)).

(2) Odor

Whether or not a surfactant had an odor was examined by the following sensory test. The surfactant composition obtained in each of Examples and Comparative Examples was taken in a 50 ml glass container, and heated in a hot-water bath at 50° C. for 30 minutes, and five persons then determined whether or not there was an odor. The surfactant composition was rated × when the number of persons smelling an odor was 2 or more, and the surfactant composition was rated ○ when the number of persons smelling an odor was 1 or less.

TABLE 1

| | Carbon number distribution in mixture of saturated aliphatic hydrocarbons (mass%) | EO | HLB | ⊿Z(%) | Evaluation (1) Detergency Evaluation | Evaluation (2) Odor Odor | Evaluation |
|---|---|---|---|---|---|---|---|
| Example 1 | 12/13/14 = 10/20/70 | 9.4 mol | 13.3 | 31.4 | ◎ | ○ | ○ |
| Comparative Example 1 | 12/13/14 = 20/55/25 | 9.0 mol | 13.3 | 27.4 | Δ | X | X |
| Comparative Example 2 | 12/13/14 = 70/20/10 | 8.6 mol | 13.3 | 25.1 | X | X | X |

Thus, as the third invention, the following embodiments are provided.

[1.]

A surfactant composition comprising: a C12 compound of the following formula (1):

[Formula 1]

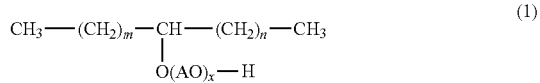

$$CH_3-(CH_2)_m-\underset{\underset{H}{|}}{\underset{O(AO)_x}{CH}}-(CH_2)_n-CH_3 \quad (1)$$

where A is an alkylene group having 1 to 3 carbon atoms, x is 1 to 50, and m+n is 9; a C13 compound of the formula (1), where A is an alkylene group having 1 to 3 carbon atoms, x is 1 to 50, and m+n is 10; and a C14 compound of the formula (1), where A is an alkylene group having 1 to 3 carbon atoms, x is 1 to 50, and m+n is 11, wherein the content of the C12 compound is 0 to 25 mass %, the content of the C13 compound is 0 to 40 mass %, and the content of the C14 compound is more than 49.9 mass % and 100 mass % or less.

[2.]

The surfactant composition according to [1.], wherein the alkylene group is an ethylene group.

[3.]

The surfactant composition according to [1.] or [2.], wherein the content of the C14 compound is 50 mass % or more.

[4.]

A method for producing a surfactant composition, comprising adding an alkylene oxide to a secondary alcohol mixture containing: 0 to 25 mass % of a C12 precursor of the following formula (2):

[Formula 2]

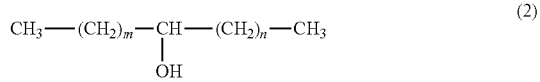

$$CH_3-(CH_2)_m-\underset{\underset{}{|}}{\underset{OH}{CH}}-(CH_2)_n-CH_3 \quad (2)$$

where m+n is 9; 0 to 40 mass % of a C13 precursor of the formula (2), where m+n is 10; and more than 49.9 mass % and 100 mass % or less of a C14 precursor of the formula (2), where m+n is 11.

The present application claims priority to Japanese Patent Application No. 2019-173623, Japanese Patent Application No. 2019-173624 and Japanese Patent Application No. 2019-173625 each filed on Sep. 25, 2019, the disclosure of which is incorporated herein by reference in their entirety.

The invention claimed is:

1. A surfactant composition comprising a mixture of secondary alcohol alkoxylates comprising:
   A) from 10 to 25 mass% of a C12 compound of the following formula (1):

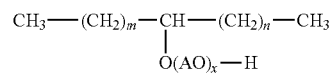

$$CH_3-(CH_2)_m-\underset{\underset{H}{|}}{\underset{O(AO)_x}{CH}}-(CH_2)_n-CH_3$$

wherein A is an alkylene group having 1 to 3 carbon atoms, x is 1 to 50, and m+n is 9;
   B) from 40 to 65 mass % of a C13 compound of the formula (1), where A is an alkylene group having 1 to 3 carbon atoms, x is 1 to 50, and m+n is 10;
   C) from 20 to 49.9 mass % of a C14 compound of the formula (1), where A is an alkylene group having 1 to 3 carbon atoms, x is 1 to 50, and m+n is 11; and
   D) a Y compound of the formula (1), where A is an alkylene group having 1 to 3 carbon atoms, x is 1 to 50, and m+n is either 8 or less and/or 12 or more, wherein 0.1 mass% ≤ $M_Y$ < 5 mass% is satisfied, and $M_Y$ is the content of the Y compound.

2. The surfactant composition according to claim 1, wherein the alkylene group is an ethylene group.

3. The surfactant composition according to claim 1, wherein the content of the Y compound is 0.4 to 4.0 mass %.

4. The surfactant composition according to claim 1, wherein m+n is at least one selected from the group consisting of 7, 8, 12 and 13 in the Y compound.

5. The surfactant composition according to claim 4, wherein m+n is at least one selected from the group consisting of 8 and 12.

6. The surfactant composition according to claim 5, wherein the content of a C11 compound with m+n being 8 is more than 0.3 mass % and 3.0 mass % or less, and the content of a C15 compound with m+n being 12 is less than 1.6 mass %.

7. A method for producing a surfactant composition, comprising adding an alkylene oxide to a secondary alcohol mixture containing:
   10 to 25 mass % of a C12 precursor of the following formula (2):

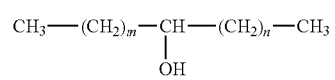

$$CH_3-(CH_2)_m-\underset{\underset{}{|}}{\underset{OH}{CH}}-(CH_2)_n-CH_3 \quad (2)$$

where m+n is 9;
   40 to 65 mass % of a C13 precursor of the formula (2), where m+n is 10;

20 to 49.9 mass % of a C14 precursor of the formula (2), where m+n is 11; and 0.1 mass % or more and less than 5 mass % of a Y precursor of the formula (2), where m+n is at least one of 8 or less and 12 or more.

* * * * *